(12) United States Patent
Rahe-Meyer

(10) Patent No.: US 7,431,702 B2
(45) Date of Patent: Oct. 7, 2008

(54) DEVICE FOR EXAMINATION OF THE MOTOR SYSTEM OF THE HUMAN OR ANIMAL BODY

(76) Inventor: Niels Rahe-Meyer, Richard-Wagner-Strasse 3, 30177 Hannover (DE)

( * ) Notice: Subject to any disclaimer, the term of this patent is extended or adjusted under 35 U.S.C. 154(b) by 0 days.

(21) Appl. No.: 10/484,739

(22) PCT Filed: Jul. 24, 2002

(86) PCT No.: PCT/DE02/02717

§ 371 (c)(1), (2), (4) Date: Jul. 9, 2004

(87) PCT Pub. No.: WO03/011137

PCT Pub. Date: Feb. 13, 2003

(65) Prior Publication Data

US 2004/0254498 A1 Dec. 16, 2004

(30) Foreign Application Priority Data

Jul. 26, 2001 (DE) ................................ 101 36 310

(51) Int. Cl.
*A61B 5/103* (2006.01)
(52) U.S. Cl. ..................................................... 600/587
(58) Field of Classification Search ................. 600/587, 600/595; 601/26; 73/862.044, 862.045, 73/760, 172, 379.01; 482/4–9
See application file for complete search history.

(56) References Cited

U.S. PATENT DOCUMENTS

| 6,413,229 B1 * | 7/2002 | Kramer et al. | 600/595 |
| 6,743,187 B2 * | 6/2004 | Solomon et al. | 600/587 |
| 6,780,142 B1 * | 8/2004 | Takizawa et al. | 482/8 |

FOREIGN PATENT DOCUMENTS

EP     0 232 507 B1    6/1991

\* cited by examiner

*Primary Examiner*—Max Hindenburg
*Assistant Examiner*—Fangemonique Smith
(74) *Attorney, Agent, or Firm*—Michael J. Striker

(57) ABSTRACT

A device for examination of motor system of human or animal body, through examination and determination of the ability of muscular system to function and perform, include a unit to insert, rest and secure body parts to be examined, and to repeat examinations of the same body parts in a same fixed position, a power source to put weight on muscle and a unit to stimulate or contract the muscles or nerves, a rest and securing element with a splint rest or with an arm rest table, a thumb mould with thumb bridge and a thumb lever, in which the thumb lever is firmly connected to a vertically arranged main unit axle, which connects to the power source; means for determining the type of contraction, to automatically limit the power via stopping mechanism, as well as stimulants for stimulation of muscles, nerves or the central nervous system, mechanical and electrical/electronic measuring devices including dynamometers, acceleration meters, muscle-length meters, sensors for the recording of electrical potential fluctuations, the skin temperature and acoustic signals and vibrations.

50 Claims, 19 Drawing Sheets

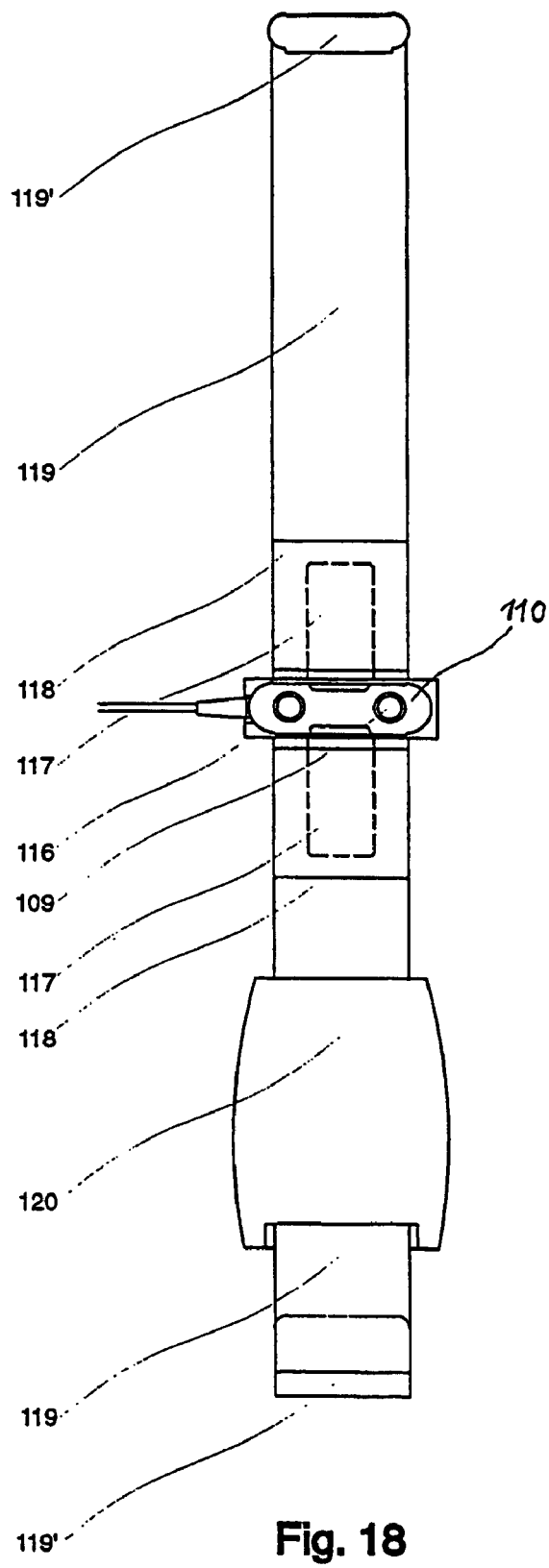
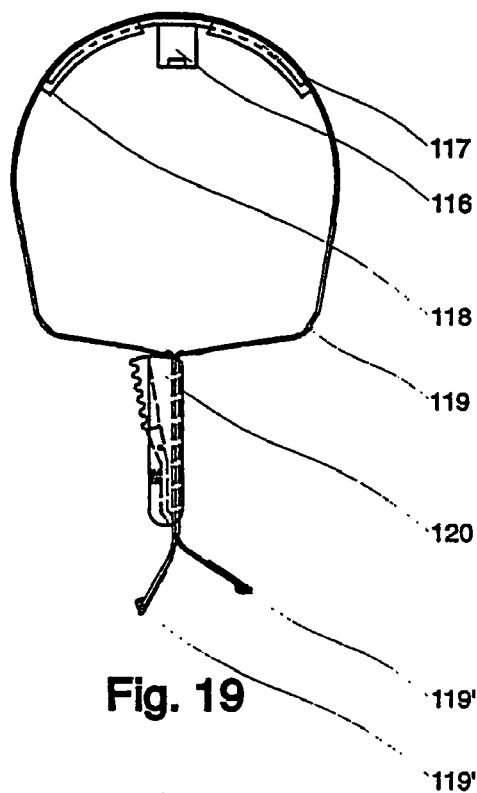
Fig. 19
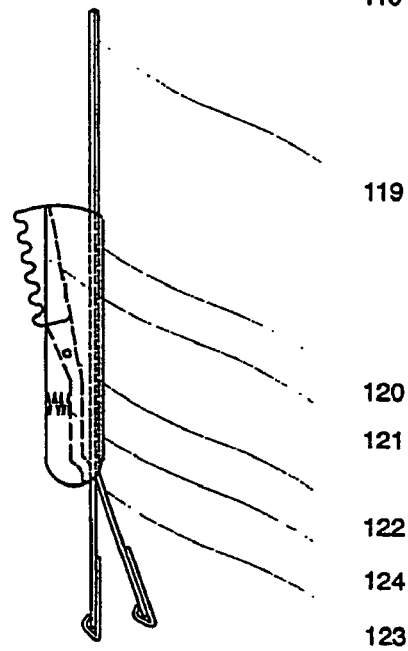
Fig. 18          Fig. 20

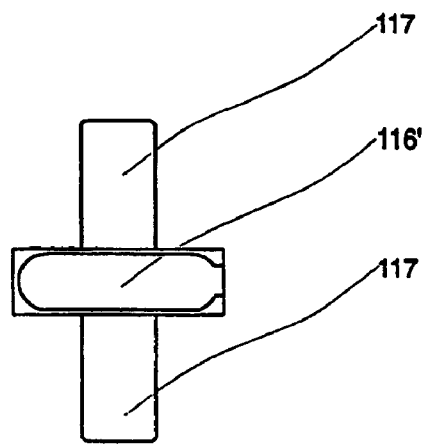
Fig. 23
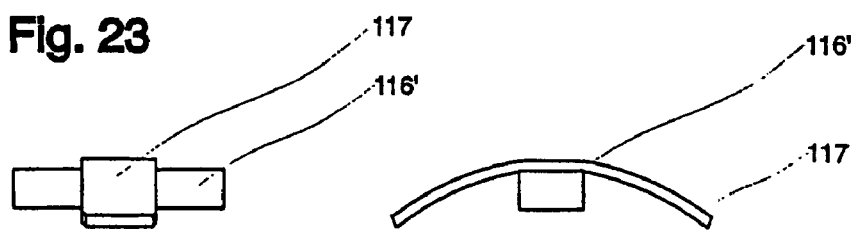
Fig. 24  Fig. 25
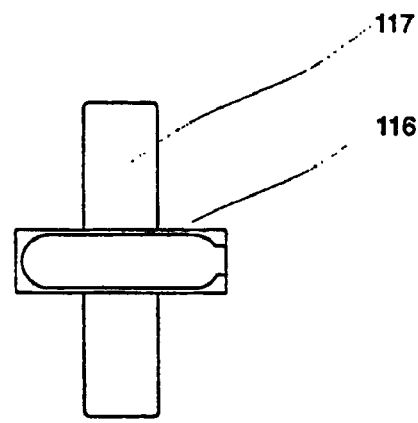
Fig. 26
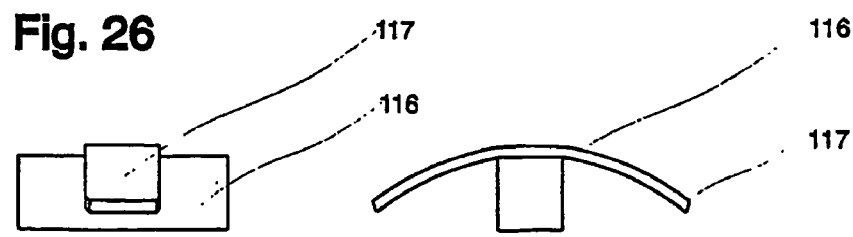
Fig. 27  Fig. 28

DEVICE FOR EXAMINATION OF THE MOTOR SYSTEM OF THE HUMAN OR ANIMAL BODY

This invention is a device for the examination of the motor system of human and animal bodies, especially of the muscular system's ability to function and perform, according to the generic term of the Patent Claim 1. The functioning of the muscles is for the individual, especially humans, a necessary requirement, in order to be able to be in contact with the outside world and to have an influence upon it. It is therefore of great importance to be able to examine the motor system and to be able to carry out objective and reliable measurements and to achieve results with the highest possible accuracy. This is, for example, of the utmost importance for the diagnosis and observation of the course of an illness to the body's ability to move and, furthermore, to name muscular illnesses, or illnesses which are secondarily connected to the influence of the motor system's ability to function; it is of further importance to the observation of the course of rehabilitation programmes, or of exercise programmes, or of the dosage control of muscle-effective medication. For this, it is very important, that examinations on the respective individual and on the same area of the body, are made to be repeated under identical conditions, as only through these means can objectivity, reliability and validity of the results be reached.

There are different devices and processes known for testing muscles and for measuring or ascertaining results and values of motion processes and of physical strength or muscle strength. However they have, amongst others, the considerable disadvantage, that an individual adjustment of the body areas to be examined, especially of the limbs, by the person examining them, is not possible and also no fixed setting of these areas takes place, at least none, which are reliable enough. Furthermore, there are no means for adjusting muscle-length conditions and few methods for the restriction of muscle-length changes with the well-known devices.

From the EP 0232507 B1 of the Applicant, there is a device known, with which the body's ability to move is being influenced by artificial stimulations and different weights and thereby nerve and muscle functions are being measured. This device has already avoided the major disadvantages of the previous devices and has itself been proven in use with the healthy and the ill. However, disadvantages have emerged. It is not, for example, possible with this known device, to standardise and make objective the examination conditions nor to pin down the object under examination and the examination results from the first examination of that individual, whilst remaining free from potential sources of error, to the point where the resulting measurements absolutely characterise the muscle mechanics of the patient being examined and to therefore make it possible to repeat similar examinations.

In particular it is not yet possible with this early invention to always set the muscle length in the same position when repeating examinations and measurements. The energy source, according to EP 0232507 B1, is also not consistent, not efficient enough and not maintenance-free enough to rule out inaccuracies or disruptions during the course of the procedure. The purpose of the this invention is, therefore, to create a device for examining the whole motor system of human and animal bodies, through which repeatable, definable and constant procedures of intervention and repeatable, absolute measurements of the motor system and especially the muscles are made possible, whilst achieving repeatable, adjustable, but, at the same time, variable muscle-length conditions through an individually adaptable splint setting device, a stopping device and power restraint mechanism, as well as through suitable measuring equipment and positioning requirement elements.

This task is in the main being solved through the characteristic features of the Patent Claim 1. Further developments and improvements of this apparatus are the subject of the further patent claims.

Examples of the implementations of the invention are explained below, using drawings.

FIG. 1 shows: the invention's examination device in side view with the casing panel removed and with the version of the rest- and securing elements set for the hand and upper wrist (see the upper area of drawing), the axle stopping device of the main unit axle with front and back rotation stopping device (middle area of drawing), as well as a power source in the form of rotating magnets with an adjustment device (lower part);

FIG. 18 shows: a mounting device for the stimulation electrodes on the examination object, as a detailed drawing;

FIG. 19 shows: the mounting device as in FIG. 18 with an adjustable fastener and clasp, viewed from the side;

FIG. 20 shows: a detail from FIG. 19, a section of the adjustable fastener with the clasp;

FIG. 23 shows: a detail of the mounting device as in FIG. 18 for the stimulation Electrodes; a small, mounting block for the stimulation electrodes with the height altered and mounting lip, viewed from the top;

FIG. 24 shows: the mounting device as in FIG. 23, viewed from the front;

FIG. 25 shows: the mounting device as in FIG. 23, viewed from the side;

FIG. 26 shows: the mounting device as in FIG. 23 with the small mounting block, which has been altered in height;

FIG. 27 shows: the mounting device as in FIG. 26 viewed from the front;

FIG. 28 shows: the mounting device as in FIG. 26 view from the side;

Figure 1:
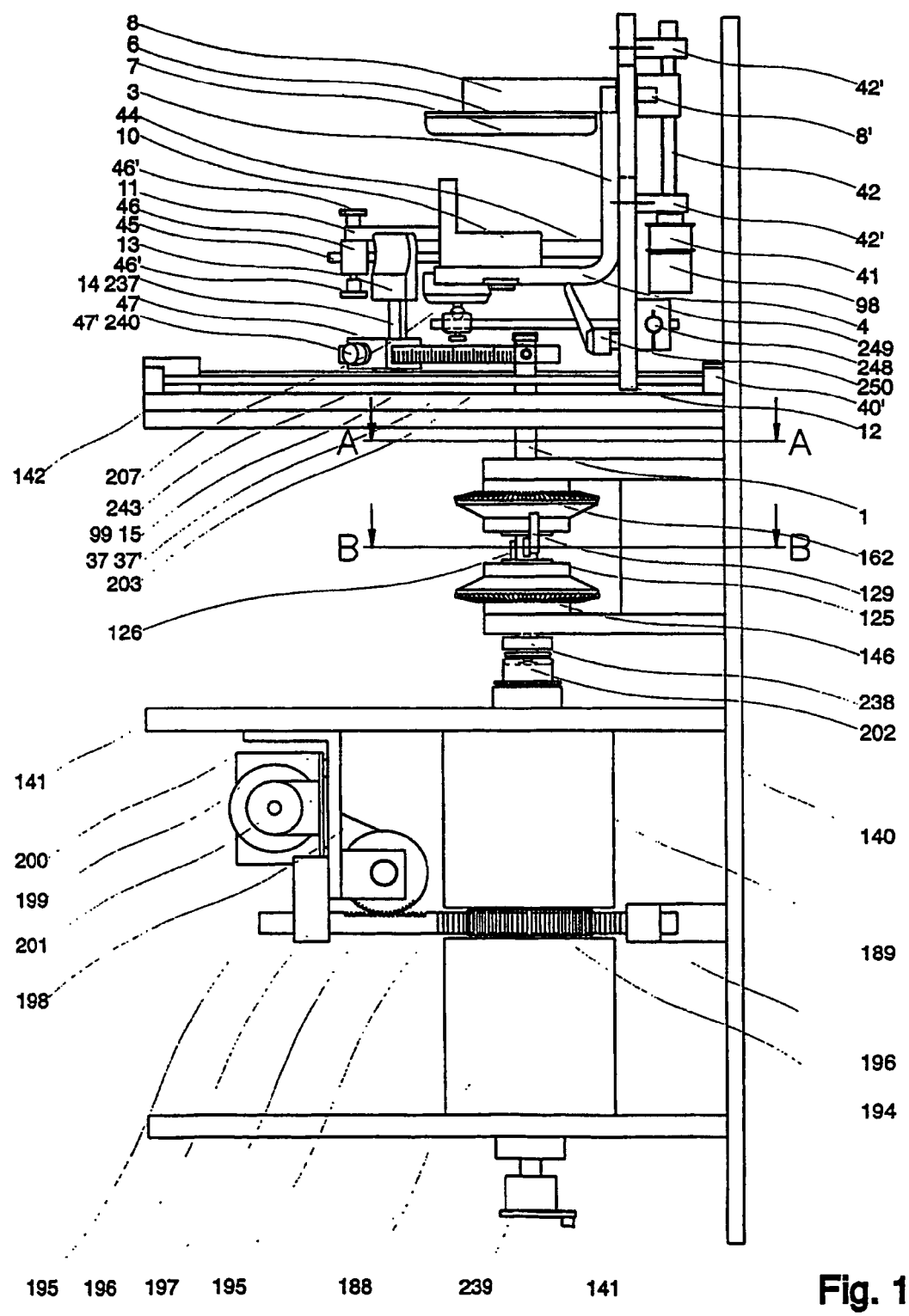
Figure 2:
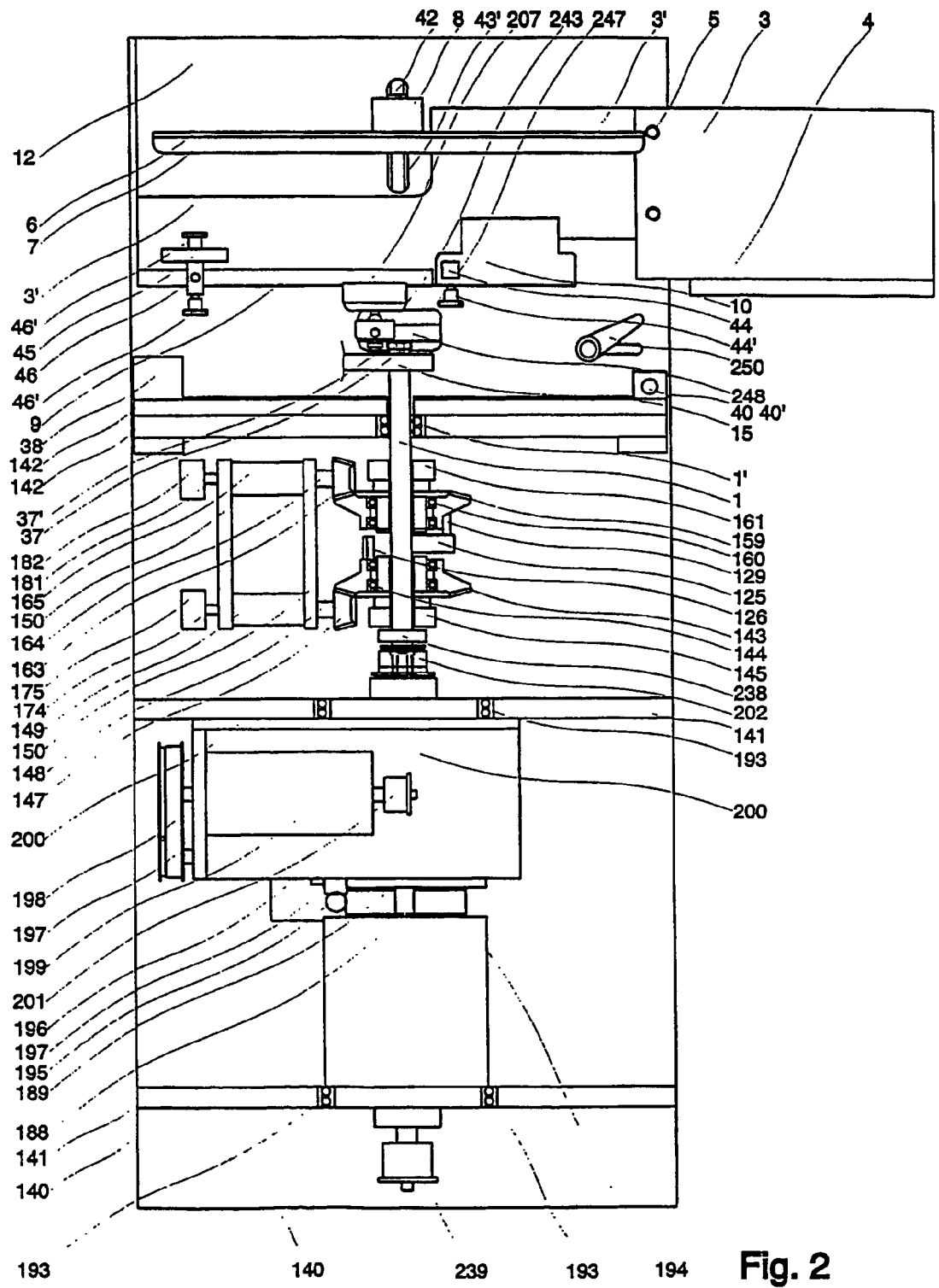
FIG. 2 shows: the examination device according to FIG. 1 as viewed from the front with the covering removed and lengthways, along the section in the area of the main unit axle.

The version of the device as illustrated in FIGS. 1 and 2 is mounted on its vertical exterior wall, labelled as "140" (which is only shown in parts). In its upper part, fitted to one of the diagonal casing panels (142), pictured here as a double panel, there is a rest- and securing element (labelled as 3, 3', 4, 6, 7, 9) for the hand, wrist and forearm to be examined. Fitted parallel to the exterior wall (140), running vertically to the dividing wall (142), is a splint rest (12) with an arm rest (3) attached to it, which continues at the same level into the hand rest (3'). At a right angle to the arm rest (3) and the splint rest (12), is the support for the back of the hand (6) with a support cushion for the back of the hand (7) and an adjustable bridge (8), which is vertically adjustable via the adjustable bridge (8) in an adapted slot (43') of the splint rest (12).

The arm rest (4) is also connected at a right angle to the arm rest (3) and the splint rest (12). Furthermore, on the hand rest (3'), there is the wrist support (10), which is horizontally adjustable by means of a support and adjustment track (44), via a fastening screw (44'), which can be locked off, so that the wrist can be supported and secured from underneath. To examine the motor system of the hand, a patient places their hand and forearm into the device, in such a way that the forearm rests on its outer side on the arm rest (3) and the wrist and the narrow side of the hand, including the small finger, rest on the hand rest (3'). The back of the hand, therefore, rests on the back of the hand support (6); the palm of the hand on the palm of the hand support (9) and the wrist rests with its underside on the wrist support (10). The fingers II-V are additionally supported at the outer edge of the index finger through a finger support (11) with a small adjustment block (46).

After the hand and the wrist have been placed in the device, they will be secured into the required position; the back of the hand support (6) and back of the hand cushion (7) will be adjusted vertically with an electrical motor (41) and spindle (42), into which the adjustable bridge meshes by means of the small adjustment block (43); also the wrist support (10) will be horizontally adjusted on the adjustment track (44) and then the appropriate positioning, which has been matched to the wrist, will be secured with the adjusting screw (44'); the top of the wrist will also be supported. The motor (41) and the spindle (42) are placed on the side facing away from the splint rest (12) and the arm rest (3), positioned by means of the spindle track (42'). The motor (41) is connected to an ammeter (98), which switches the motor off as soon as the back of the hand support (6) presses against the back of the hand with a pre-set pressure limit. Additionally, the back of the hand support (6), together with the adjustable bridge (8), can be tilted over a vertical axle and rotated via a swivel coupling (8'), situated in the vicinity of the spindle. The finger support (11) will be moved towards the index finger through the adjustment block on the adjustment track (45) and then secured with the adjusting screws (46').

The splint rest (12) itself, with the fore-mentioned parts, is horizontally adjustable parallel to the dividing wall (142) on one or more tracks (40), which are fixed to the dividing wall (142) with mountings (40') and arranged as spindles, through an electrical motor (38). To examine how the muscular system of a body part or the nerve system of a body part function and perform (in the version of the device in FIGS. 1 and 2, preferably the muscles of the thumb abductor), there is a thumb mould (13) with a bridge for the inserted hand, which interlocks with the horizontal thumb lever (15) and is horizontally adjustable, through the adjustment device (47) and the locking mechanism (47'). The thumb will be placed into this thumb mould (13). The thumb lever (15) is placed on the vertical main unit axle (1), which is guided through the dividing wall (142) and an additional horizontal dividing wall (141) and connected to the rotation magnets (188) and (189) as an energy source.

Figure 3:
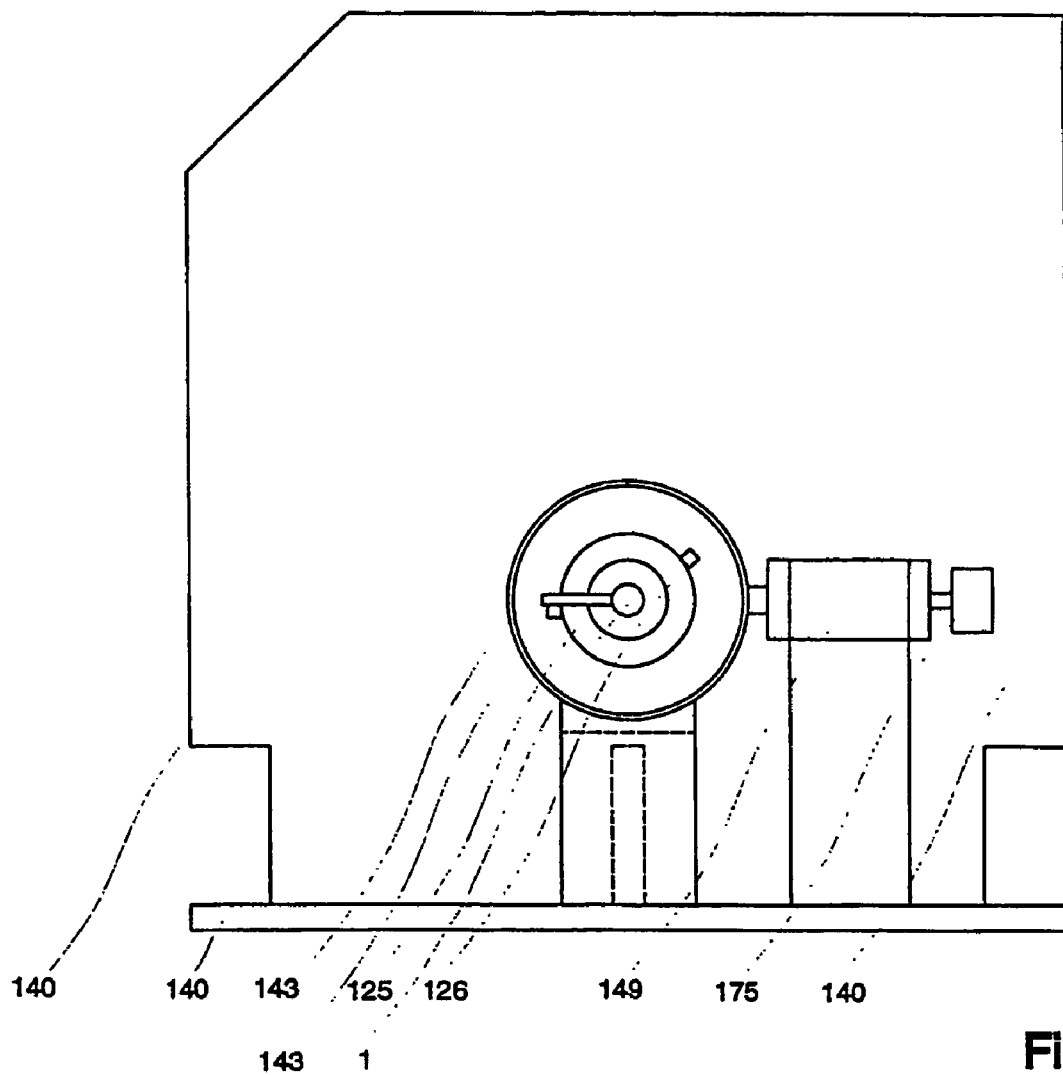
FIG. 3 shows: a detail of FIG. 1, that is, the area of the axle stopping mechanism with the front rotation stopping mechanism and the adjustment motor, as viewed from above in section B/B.
Figure 4:
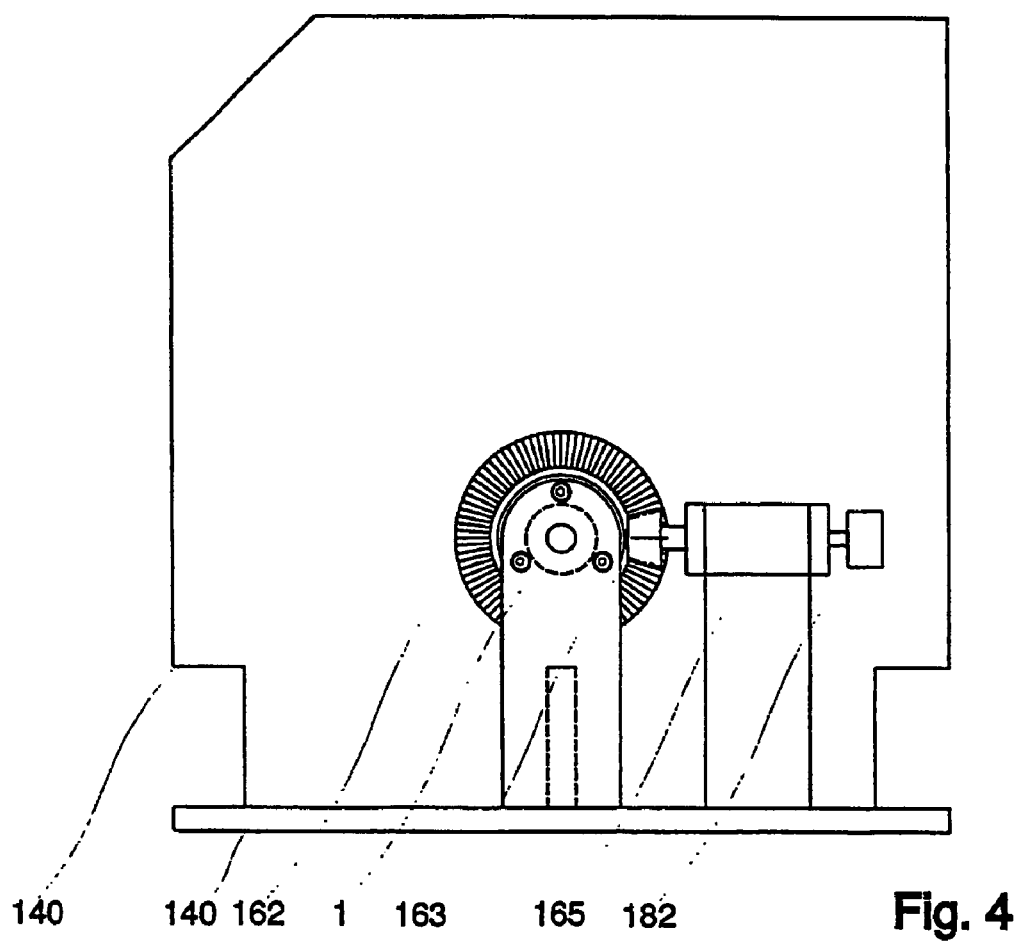
FIG. 4 shows: a detail of FIG. 1: the area of the axle stopping mechanism with back rotation stopping mechanism and adjustment motor, as viewed from above at section A/A.

On the top end of the main unit axle (1), there is a laser direction-finding beamer (37) with an aperture (37'), whose direction-finding beam will be aligned with the axle of the examined body part, for example, the movement axle of the thumb adductor and thumb abductor. The hand, wrist and forearm are secured in this position by the armrests (3) and (4), the back of the hand support (6), the palm of the hand support (9), the wrist support (10), the finger support (11), as well as the splint rest (12). The thumb is also firmly connected to the main unit axle (1) of the device through the thumb mould (13) and the thumb lever (15). As an energy source, the rotation magnets (188) and (189) exert a defined load, through the main unit axle 1 and the thumb lever (15) on the to be examined muscles of the patient, either before or after lifting. As is also visible in FIGS. 1 and 2, and shown in detail in FIGS. 3 and 4, the main unit axle (1) has a firmly connected axle stopping mechanism (125) below the dividing wall (142), which works together with a rotation stopping mechanism (126) (see FIGS. 1 to 3). The rotation stopping mechanism (126) is fixed to an adjustable wheel (143), through which the angle can be altered. The adjustable wheel (143) rests on a guide rod through a bearing (144), which grips the main unit axle (1) without pressure. The adjustable wheel (143) is, on the far side of the stopping mechanism, further equipped with a sprocket (146), slotting into a cog wheel (163), that is driven by an axle (164) of an adjustable motor (149), which is fixed onto the casing (140) by means of mountings (150). A potentiometer (175) is fixed to the motor axle (164) via the potentiometer axle (174), which measures the position of the front stopping mechanism. The front rotation stopping mechanism (126) cuts down rotation movements of the thumb lever (15) beyond this point and thereby contractions of the thumb adductor, so that isometric spasms or touch spasms can be inflicted at a defined muscle length.

The axle stopping mechanism (125) works together with a back rotation stopping mechanism (129). It is fitted onto an adjustable wheel (159) and can through this also be adjusted in its angle. The adjustment wheel (159) rests analogous to the fine-tuning of the front rotation stopping mechanism via a bearing (160) on the guiding rod (161), which grips the main unit axle (1) without pressure. The adjustment wheel (159), on the far side of the stopping mechanism, is further equipped with a sprocket (162), into which a cog wheel (163') meshes, that is driven by an axle (164') of an adjustable motor (165), which is fixed to the casing (140) by means of mountings (150). A potentiometer (182) is also fixed to the motor axle (164') by the potentiometer axle (181), which measures the position of the rear stopping mechanism. Rotation movements of the thumb lever (15) towards the back will be prevented through the rear rotation stopping mechanism (129), thereby stretching the thumb adductor, so that support spasms can be triggered on a defined muscle length.

For putting weight on the muscles, the rotation magnets (188) and (189) are used as power sources and are switched, one after the other, and firmly placed at the top or bottom of the dividing wall (141) with the bearings (193). Their inner parts are connected to the main unit axle (1) and can rotate around these inner parts. There is a sprocket (194) between the two rotation magnets, slotting into a rack track (195), that is guided by appropriate track bearings (196) and is linear and horizontally movable. The rack track is connected to a motor (199) through a cog wheel (197) and a transmission belt (198) and is fixed to a mounting plate (200) on the top dividing wall (141). Through the cog wheel or rack track connectors (194, 195 and 197), the motor (199) regulates the rotation magnets (188) and (189) in such a way, that the area of movement of the patient being examined falls into a favourable working zone or known indicator zone of the rotation magnets. There is a potentiometer (201) on the axle of the motor (199), measuring the respective positions of the rotation magnets (188) and (189).

In order to avoid too high and therefore damaging pressure on the examined limbs, a slip clutch mechanism (202) that can be electronically steered and adjusted within its working area, which is placed on the main unit axle (1), connecting with the rotation magnets (188) and (189). Instead of the slip clutch mechanism, or in addition to it, the connection between the thumb lever (15) with the main unit axle (1), as can be seen in FIG. 1, can be made in a simpler way by using a pin (203) with a predefined breaking point, which will break when a defined limit of the power source (188 and 189) is exceeded; therefore no further pressure can be exerted on the secured thumb of the person being tested.

Another version of the invention device is shown in FIG. 5 to 8. This version is also mounted on its vertical exterior walls (140) - this is only partially visible on the drawing. A horizontally movable arm rest table (16) is fixed to the diagonal casing panel (142), set vertically above it, in guiding tracks or supports (58) on at least two of the outer sides of the diagonal casing panel (142), lying opposite each other, upon which the arm and hand can be rested and secured for examination. The arm rest table (16) has a cut out section (16'), in which a thumb mould (23) with bridge (24) protrudes from the thumb lever (25), situated below the arm rest table (16) (according to the thumb mould (13) with bridge (14) and thumb lever (15)) running vertically to the top, for the thumb of the inserted hand to fit in it. The thumb lever (25) is fitted to the vertical main unit axle (1), as in the version in Fig 1 and 2, which on her part is guided by the double diagonal casing panel (142) and the additional dividing wall (141) and then connecting into an electrical motor, preferably a Hall motor (190), as an alternative power source to the rotation magnets (188 and 189).

Fitted in the middle of the arm rest table (16), is the arm cradling unit (17), which runs lengthways to the resting arm and hand, upon which the inside of the arm and the edge of the hand are placed; depending on the examined right or left limb and, if the palm of the hand is facing up or down, either to the right or the left of the position of the arm.

The arm rest table (16) can be moved in the guide tracks (58) via a motor (56), which is installed below the arm rest table, attached to the diagonal casing panel (142), and a small adjustment block (52), fitted to the arm rest table (16) and guided in a spindle (53), by means of a transmission belt (55), so that the resting arm can be moved sideways into the correct position. The spindle (53) itself rests in the guide tracks (54) on the underside of the arm rest table (16). The position of the arm rest table (16) can be measured via a linear meter (100), which is connected to the small adjustment block (52) through the connector (101), so that later examinations can be repeatedly determined.

Figure 5:
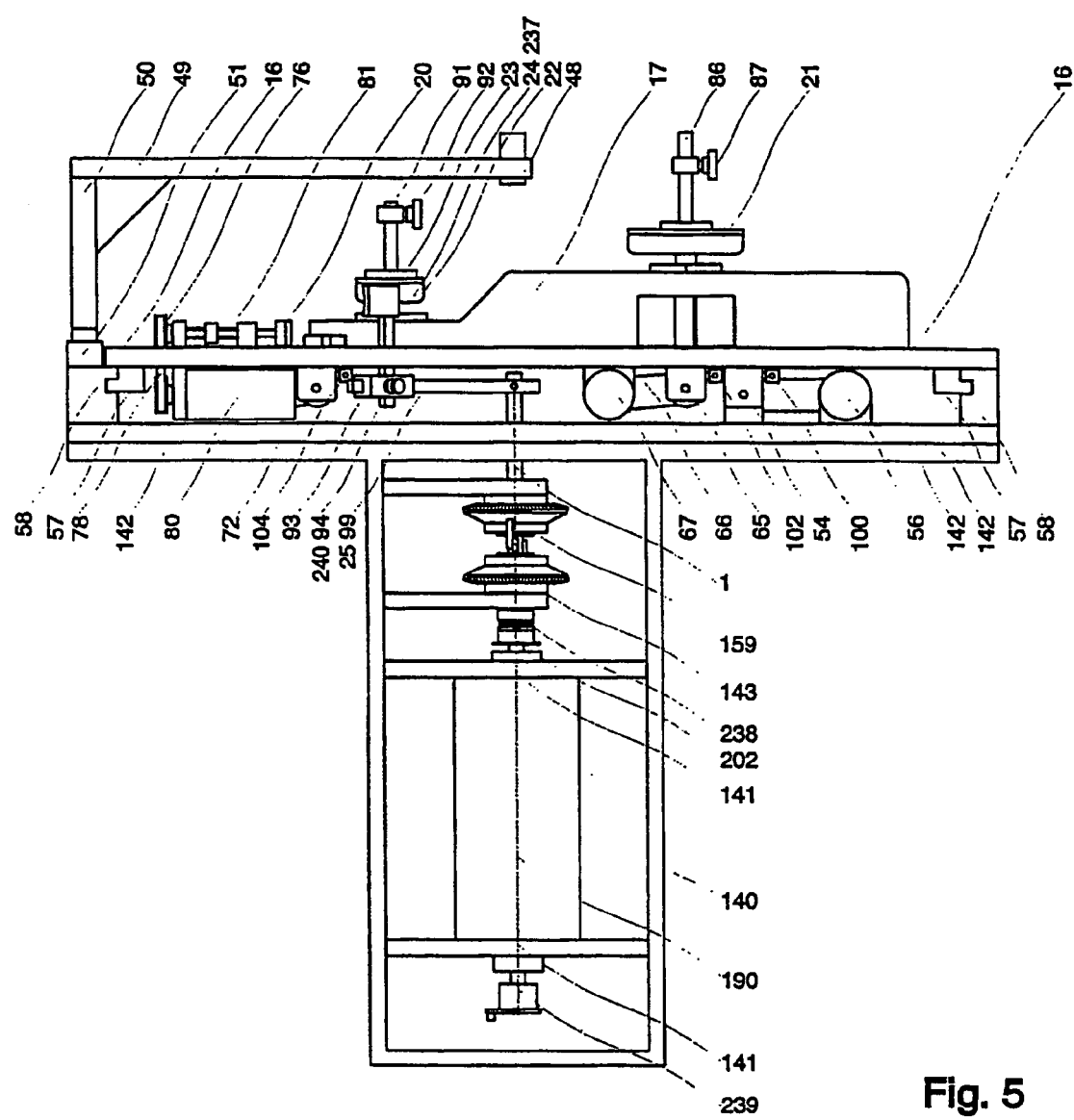
FIG. 5 shows: the examination device with an altered rest- and securing element for the arm and wrist, as well as the power source in the form of an electric motor, viewed from the side with the side panel removed.
Figure 6:
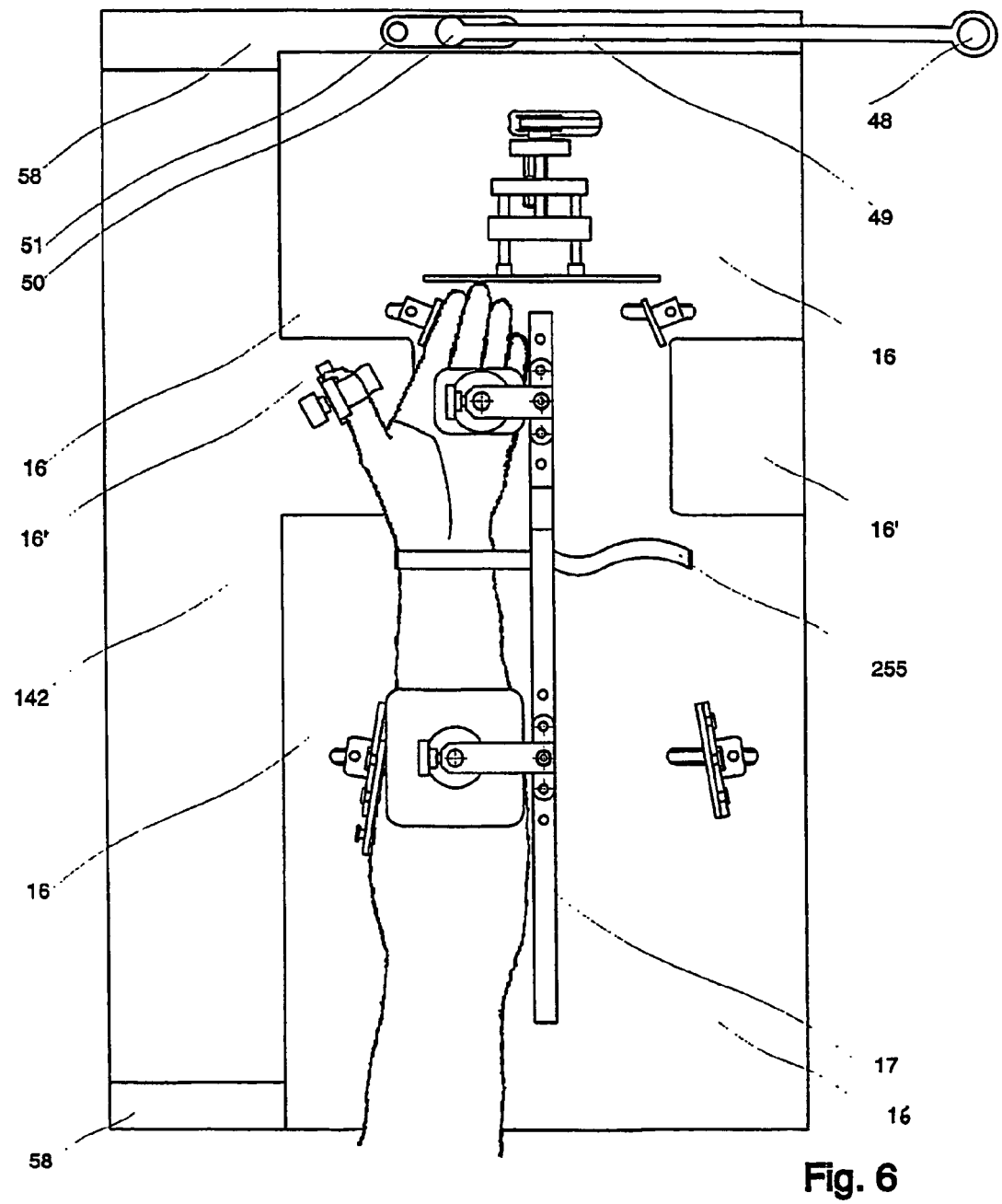
FIG. 6 shows: the altered rest- and securing element as detailed in FIG. 5, but from the right, viewed from above, with a hand and arm inserted and secured.
Figure 7:
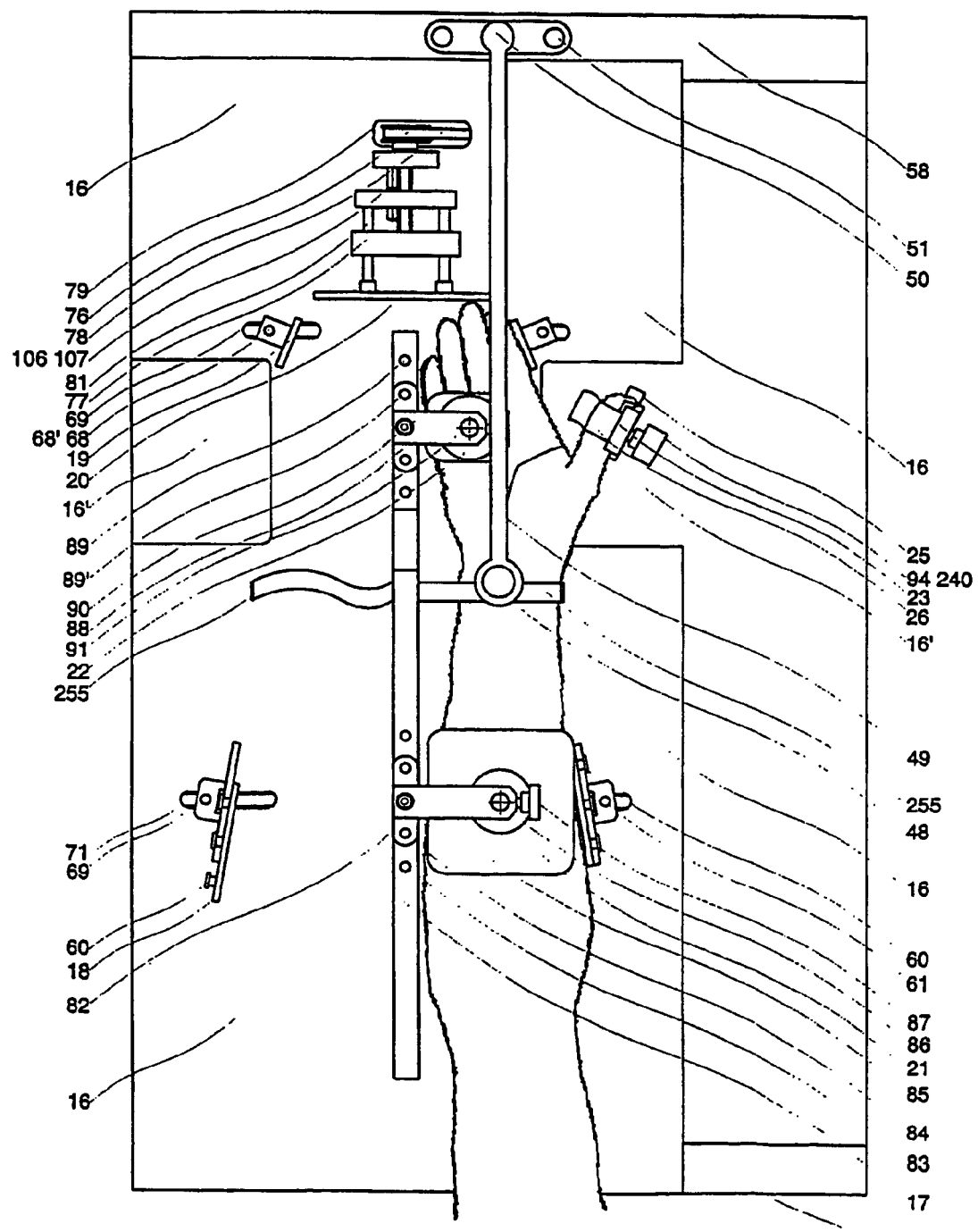
FIG. 7 shows: the altered rest- and securing element of the examination device, as in FIG. 6, but with a right arm and hand inserted.
Figure 8:
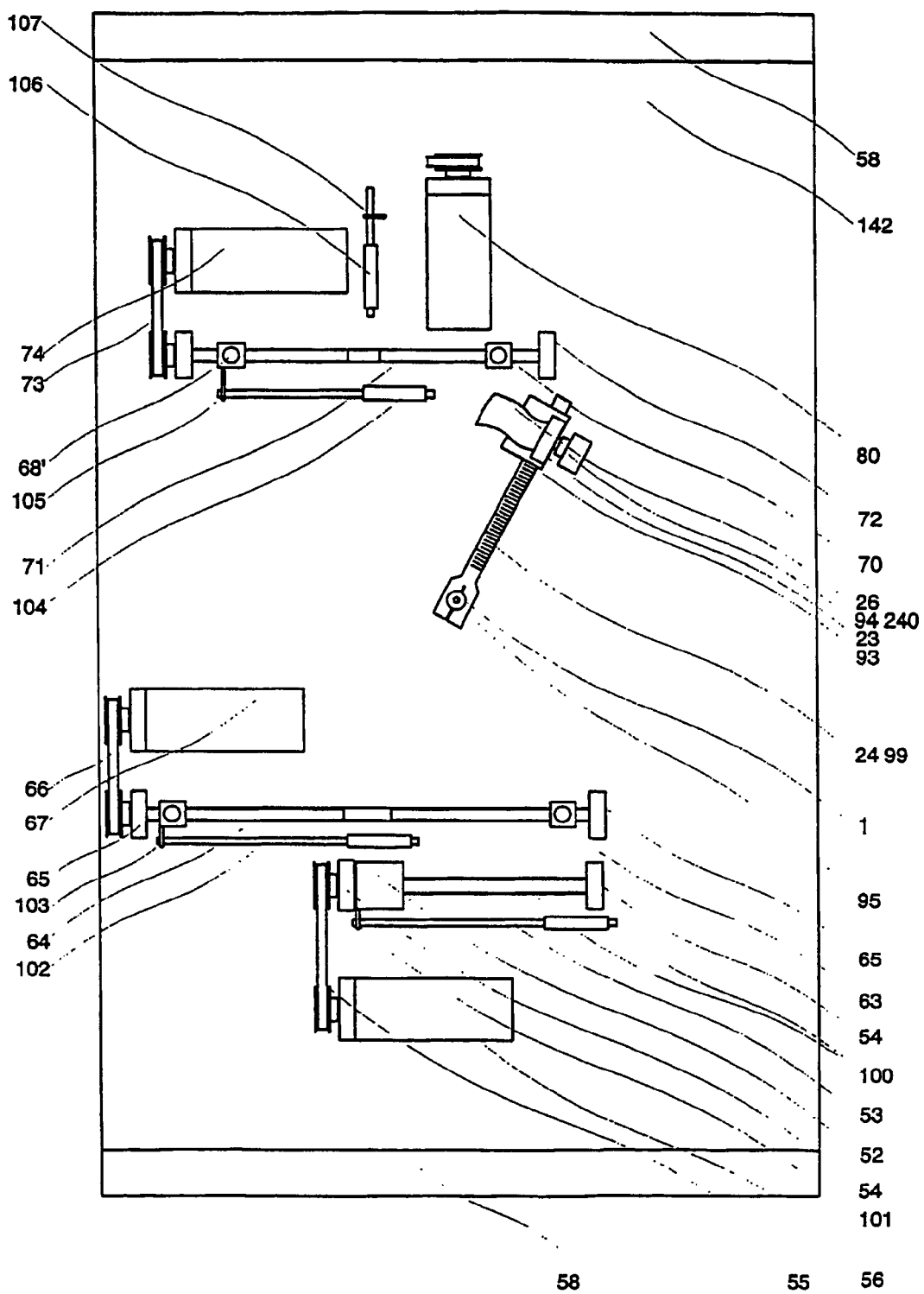
FIG. 8 shows: the rest- and securing element as in FIG. 5 from above after the removal of the arm rest table, looking at it from the exterior on the right.
Figure 9:
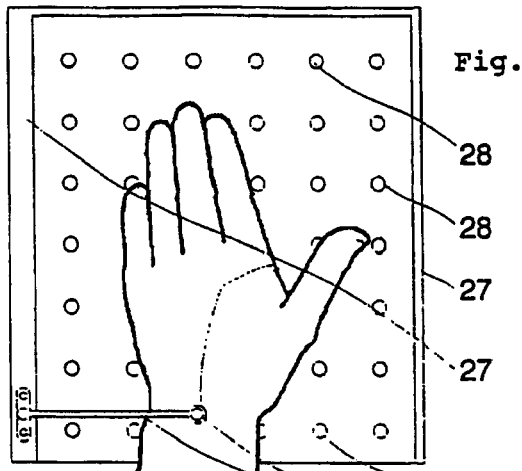
FIG. 9 shows: a modified part of the rest- and securing element/setting as in FIG. 5; a mould with spacing pins for the making of a cast, which serves as a securing element for the hand, being the examination object.
Figure 12:
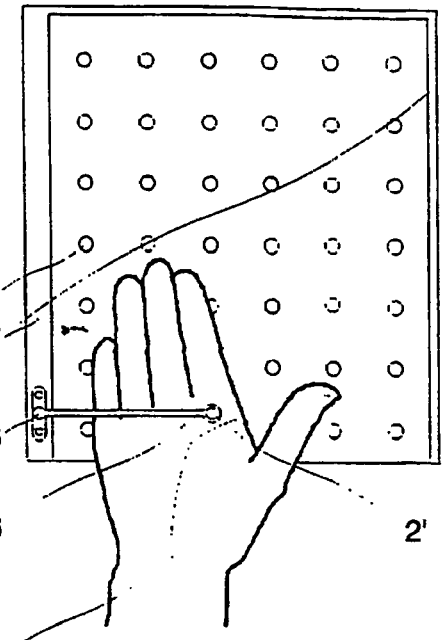
FIG. 12 shows: the mould as in FIG. 9, viewed from above, showing a hand placed upon it.
Figure 10:
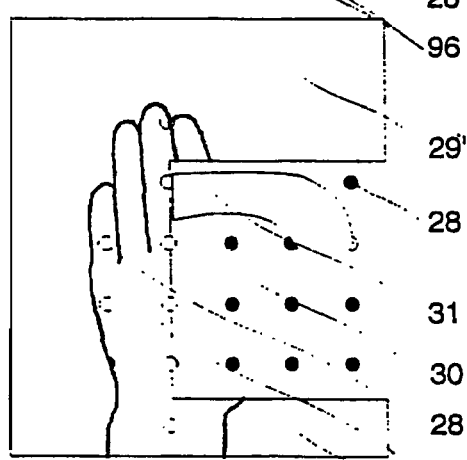
FIG. 10 shows: the cast made with the mould as in FIG. 9, with cut-out area for the thumb, mounted on the arm rest table as in FIG. 5, viewed from the top.
Figure 11:
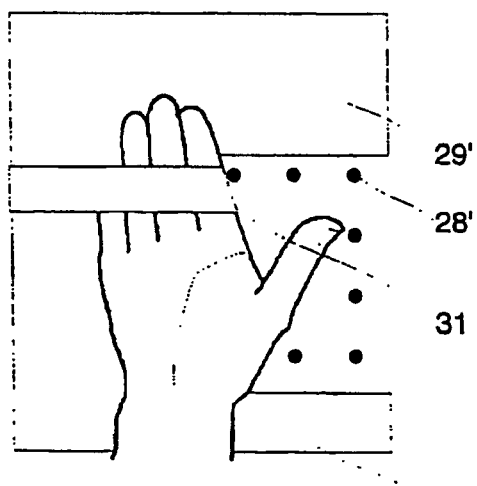
FIG. 11 shows: the cast serving as a securing element as in FIG. 10 with an inserted and secured hand.

Here too, the motion axle of the examined body part is being brought in alignment with the direction-finding beam of the laser direction-finding beamer (37), in order to bring the body part being examined into the correct position. Alternatively, or in addition to the laser direction-finding beamer (37), as shown in FIGS. 5 to 7, the laser direction-finding beamer can be on a swivel arm (49), which is fixed on the exterior dividing wall (142) on a guide track (58) and rotates, which will be swivelled over the arm rest table and the resting limb. The movement axle of the examined body part will then be aligned with the beam of the direction-finding beamer (48), which points down vertically and in which the directional beam exactly corresponds with the main unit axle (1). The arm will be secured in this position with the arm clamp cushion (21) and the palm of the hand cushion (22), in which the arm clamp cushion (21) is attached with a clamp (85) and the palm of the hand cushion (22) and is attached with a clamp (90) at the upper side of the arm rest through clamp fastenings (82) and (88). The fastening takes place in the known manner through screws or bolts (84) and (89') in drill holes (83) and (89). The clamps (85) and (90) are each adjustable lengthways towards the arm rest, so that it can be adjusted to any anatomical condition of the person being tested, by providing a row of holes (83) and (89) in the arm rest (17). The arm clamp cushion (21) and the palm of the hand cushion (22) can each be rotated by 180° and placed and secured in the arm rest (17), depending on which limb is being examined. To enable an adjustment of the arm clamp cushion and the palm of the hand cushion to the individual height of the palm of the hand and the forearm, when placed in it, the arm clamp cushion has an adjustment bar (86) with stopping mechanism (87) and the palm of the hand cushion (22) has an adjustment bar (91) with stopping mechanism (92), each attached vertically to the arm rest table (16) and vertically protruding, as well as vertically protruding the arm rest (17).

The outside of the fingers II to V, which is opposite the edge of the hand, is supported by a preferably padded finger support (19), which is also adjustable and attached to the arm rest table (16) and which has a swivel coupling (68) with swivel coupling pin (68') for adjustment to the individual finger shape. Appropriate finger supports are placed both sides of the arm rest (17), for support of the fingers of the right and left hand.

Through an elongated hole (69) on the underside of the arm rest table (16), the swivel coupling pin (68') is connected to a small adjustment block (70), which, through a spindle (71) with counter-rotating threads and a motor (74), leads the finger support (19) for setting the splint towards the inserted; at the same time the second finger support is moving in the opposite direction to the arm rest (17). The spindle (71) with spindle guide tracks (72) is attached to the underside of the arm rest table (16), the same as the motor (74), which drives the spindle via a transmission belt (73).

As with the finger supports (19), there are arm supports (18) in the area of the arm clamp cushions (21) at both sides of the arm rest (17), provided for each of the outer sides of the arms, which, in their technical composition, mainly correspond to the swivel coupling (61), the swivel coupling pin (61'), the small adjustment block (63) and the spindle (64); the arm support again leads towards the inserted arm via a motor (67) with transmission belt (66) and the spindle.

The position of the finger support (19) can be measured through a linear meter (104), which is connected through a connector (105) with the small adjustment block (70), and can thus be determined for later examinations. The position of the arm support (18) can also be measured through a linear meter (102), which is connected to the small adjustment block (63) by the connector (103), and can thus be determined for later examinations. For the support of the finger tips, there is an adjustable support (20) on the arm rest table (16), as in the example in FIGS. 5 to 8, which—as with the finger support (19)—is firmly connected to the small adjustment block (75), guided in a spindle (76) beneath the arm rest table. The spindle rests and is pivoted in the guide tracks (77) at the arm rest table and is driven by a motor (80) and a transmission belt (78); the support (20) with its telescopic guide tracks (81), is lead to the finger tips and positioned through the small adjustment block (75). The position of these finger supports (20) can also be measured through a linear meter (106), which is connected with the small adjustment block (75) via a connector (107) and can thus be determined for later examinations.

The thumb of the inserted and secured limb, will be supported from behind by the thumb mould (23), contrary to the thumb mould (13) in the example in FIGS. 1 and 2, and set with a fastener (26). In this version, the thumb bridge (24) is also horizontally adjusted on the thumb lever (25), in order to fit the size of the hand and thumb of the examined limb, and secured with the stopping mechanism (94).

In this version too, the main unit axle (1) has, below the dividing wall (142), the firmly connected axle stopping mechanism (125), the front rotation stopping mechanism (126) and the back rotation stopping mechanism (129) and their additional components, as in the version according to FIGS. 1 to 4. This version can also have the rotation magnets (188) and (189) as its power source, instead of the above mentioned Hall motor.

FIGS. 9 to 12 shows a further beneficial version of the invented device with a different rest- and securing element for the hand to be examined, which, in the version according to FIGS. 5 to 8, replaces the rest- and securing element for the hand and the arm, the arm rest (17) with arm support (18), finger support (19) and fingertip support (20), as well as the devices and versions described. The part of the limb of the person being tested, serving as the object of the examination—in the example shown, the hand—is being placed in a mould (27) with spacing pins (28), which are loosely stuck at the bottom of the mould (27). The drill holes at the bottom of the mould (27) correspond to the drill holes (28') in the arm rest table (16). On one of the top outer rims of the mould (27), is the arm with laser direction-finding beamer (96)—corresponding to the swivel arm (49, 50) with laser direction-finding beamer (48)—attached in such a way, that when the mould is put on the arm rest table (16), the direction-finding beam is pointing directly to the main unit axle (1) of the device, where the drill holes at the bottom of the mould (27) and the drill holes in the arm rest table correspond. After placing the hand or the section of the hand on the spacing pins (28) of the mould (27), the swivelling laser direction-finding beamer (96) will be swivelled over the limbs, so that the direction-finding beam corresponds with the movement axle of the person being tested. In this position, a suitable synthetic material or other pouring substance will be poured over the limb, so that the shape of the back of the hand and the fingers, as well as possibly the wrist, will be taken and an individual bed for the hand is created. The substance is also poured over the spacing pins (28); a thumb cavity (30) will be cut out of this cast (29), after it has been taken out of the mould (27). The mould with the spacing pins (28), protruding from the bottom of the synthetic material, will be inserted into the fore-mentioned drilling holes of the arm rest table (16). For examination or setting, even in the case of the process being repeated, the patient being tested simply places their hand or section of their hand into the cast (29). A fastener (31) can be provided, to further secure it in the cast. Otherwise the device corresponds with the version according to FIGS. 5 to 8, especially concerning the securing of the thumb with the thumb mould (23) and its connector via the thumb bridge (24) and the thumb lever (25) with the main unit axle (1).

Figure 13:
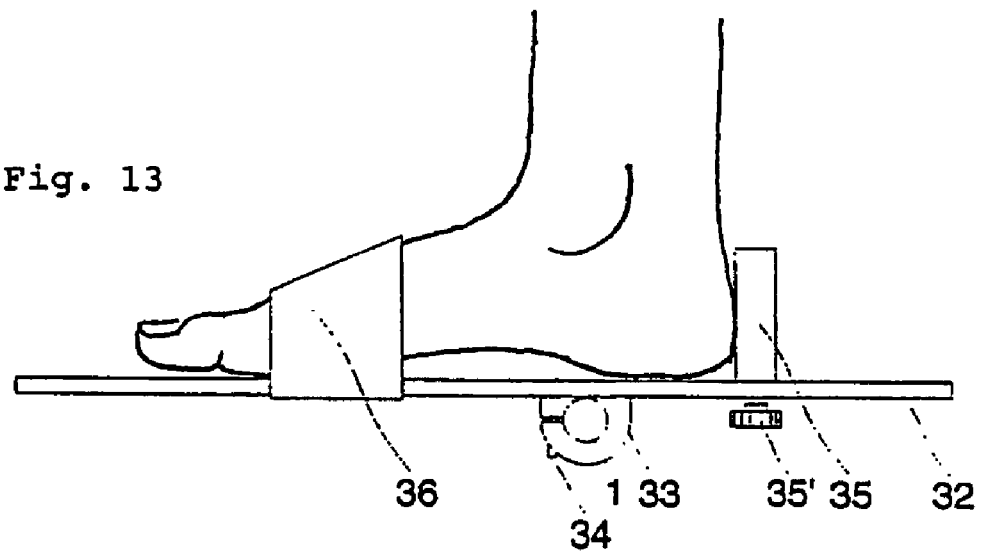
FIG. 13 shows: a further modification of the rest- and securing element, according to FIGS. 1 and 5; a rest- and securing element for a human ankle joint with a foot fixed in it, viewed from above.
Figure 14:
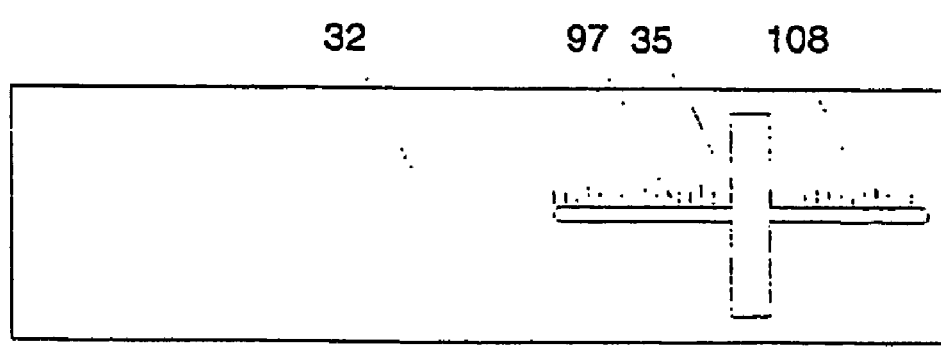
FIG. 14 shows: the rest plate of the rest- and securing element according to FIG. 13, viewed from the side, for those body areas near where the limbs meet the body.

As a variation, a rest- and fixation element for the examination of muscles is shown in FIGS. 13 and 14, which works for the larger joints, for example the upper ankle joint, the elbow joint or the knee joint. This version consists of a rest plate (32) for the ankle joint shown here; it has a fastening ring (33) on its underside, which is mounted on the main unit axle (1) and screwed down. The rest plate (32) has an elongated hole (96) over at least one part of its length, into which a support block (35), positioned on the top side of the rest plate, connects with a pin, which can be secured with a screw (35'). Once the test person has placed their foot on the support block (35), it will be secured in such a way, that the movement axle of the body part to be examined (here the ankle joint) will lie on the main unit axle of the device. Additionally, the limb will be fixed to the rest plate (32) with a fastener (36). A measuring scale (108) at the elongated hole (97) will make it possible to measure the position of the body part being examined and therefore determine the later, repeated examinations of the same object.

Figure 15:
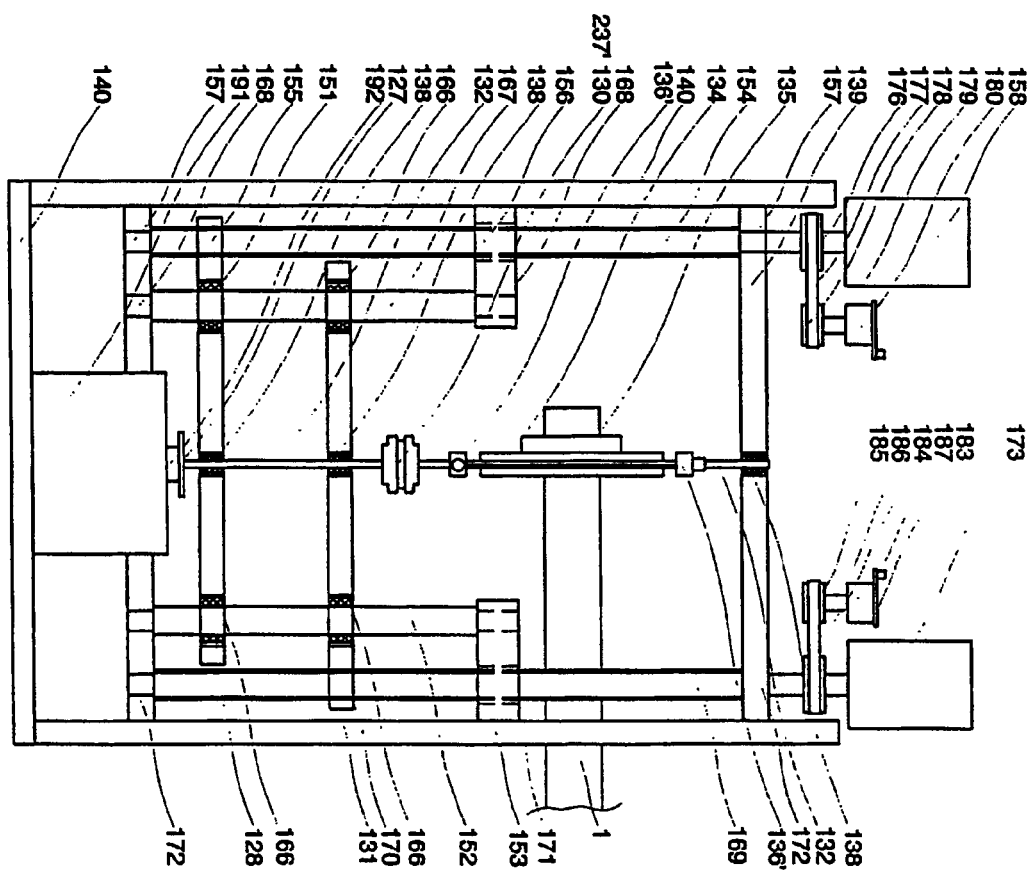
FIG. 15 shows: a modification of the examination device, powered by a linear drive with a linear axle, as in the version shown in FIGS. 1 and 5, with the front and rear linear stopping mechanism, viewed from the front with the casing panel removed.
Figure 16:
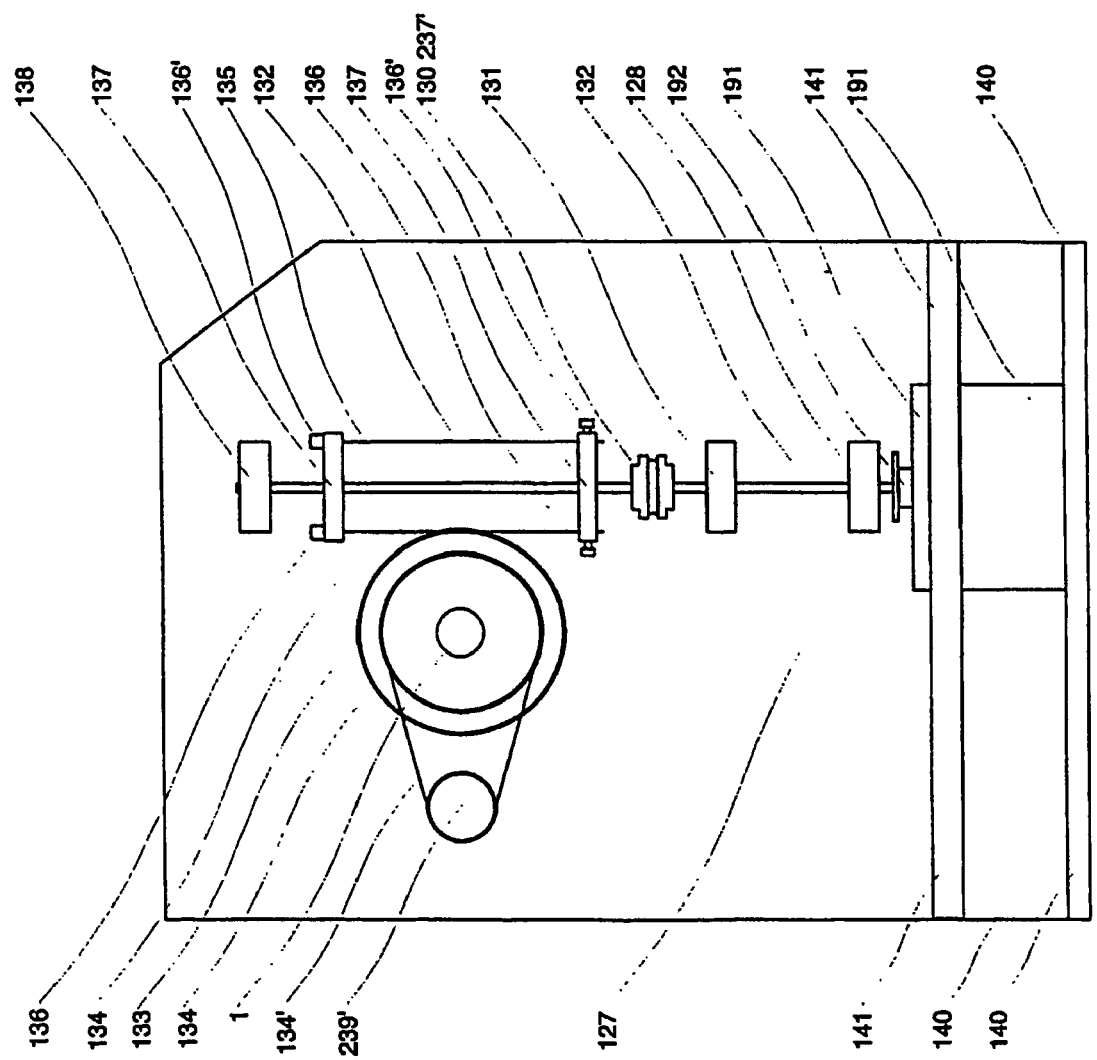
FIG. 16 shows: the alteration as in FIG. 15, viewed from the side, with the linear motor, the linear axle, linear stopping mechanism and power diverter onto the main unit axle.

A further version of the power source and the device to limit contraction and stretching of the examined muscle e.g. the thumb adductor, is shown in FIGS. 15 and 16, which replaces the version of these parts of the invented device, shown in FIGS. 1 to 4 and FIG. 5. The rest- and securing element for the to be body parts to be examined, however, is in accordance with the fore-mentioned and, in FIG. 15, joined to the top dividing wall of the casing with the visible opening of the main unit axle (1). As a power source, this version has a linear drive (191) by way of a linear motor or lifting magnet, which transmits power onto the rotating, movable main unit axle (1), via the linear axle (132) and a transmission or energy diverter (133 to 137). At the same time, there is—on the main unit axle (1), in the area where they meet with the linear axle (132)—a transmission wheel (133) and a transmission cord (134), half of which runs on the top, over the transmission wheel (133), to a lower cord clip (136) on the linear axle (132) and is being locked off; the other half runs at the bottom over the transmission wheel (133) to a higher cord clip (136) on the linear axle (132) and is locked off. On the opposite side of the linear axle (132) to the transmission cord (134), is a counter-moving cord (135), fitted with clips (136'), which are themselves attached to the linear axle (132) by clamp bridges (137), in order to avoid one-sided strain and bending of the linear axle (132).

The linear axle (132) rests, with its end opposite the motor or lifting magnet (191), on the area of the exterior casing, in a guiding rod (139) with glide bearing (138), which itself is placed on the exterior casing (140) or dividing wall (141) of the casing. Together with the linear axle (132), there is a front axle stopping mechanism (127), firmly connected to the linear drive, which also acts as a stopping mechanism for the linear axle (132), which is positioned diagonally to the linear stopping mechanism (128). This linear stopping mechanism (128) consists of a bar, through which the linear axle (132) in lead through via the glide bearing. It is guided through vertically positioned guiding rods (152 and 167) and is adjustable on these glide bearings (151 and 166), parallel to the adjustable linear axle. The guiding rods (152 and 167) are secured with fastening bars (153 and 168), firmly connected to the casing (140) or dividing wall (141). The movement occurs via a spindle (154), which runs in a thread (155) through the linear stopping mechanism (128). The linear stopping mechanism (128) is moved via the spindle (154) by means of the motor (158). In this version, with the front linear stopping mechanism (128) at the axle stopping mechanism (127), clockwise movements of the main unit axle (1) and, thereby, for example, contractions of the thumb adductors, are limited and isometric or touch spasms are forced with a defined muscle length.

Furthermore, the version shown in FIGS. 15 and 16 has a back axle stopping mechanism (130), which is firmly connected to the linear axle (132), against which a rear linear stopping mechanism (131) strikes. This rear linear stopping mechanism (131) is also guided by the guiding rods (152 and 167). It is driven by the spindle (169) with motor (173), which corresponds to the described movement of the front linear stopping mechanism (128). A potentiometer (239') is connected to the transmission wheel (133), so that the respective position of the linear axle (132) can be measured. On the linear axle (132), there is also a dynamometer (237') for measuring push and pull tension. Attached to each of the spindles (154 and 169), is a potentiometer (180 or 187) for measuring the position of the front linear stopping mechanism (128) or the rear linear stopping mechanism (131). In the version shown, this happens through transmission wheels (176 and 178) with the transmission cord (177) or through the transmission wheels (183 and 185) with the transmission cord (184).

Figure 17:
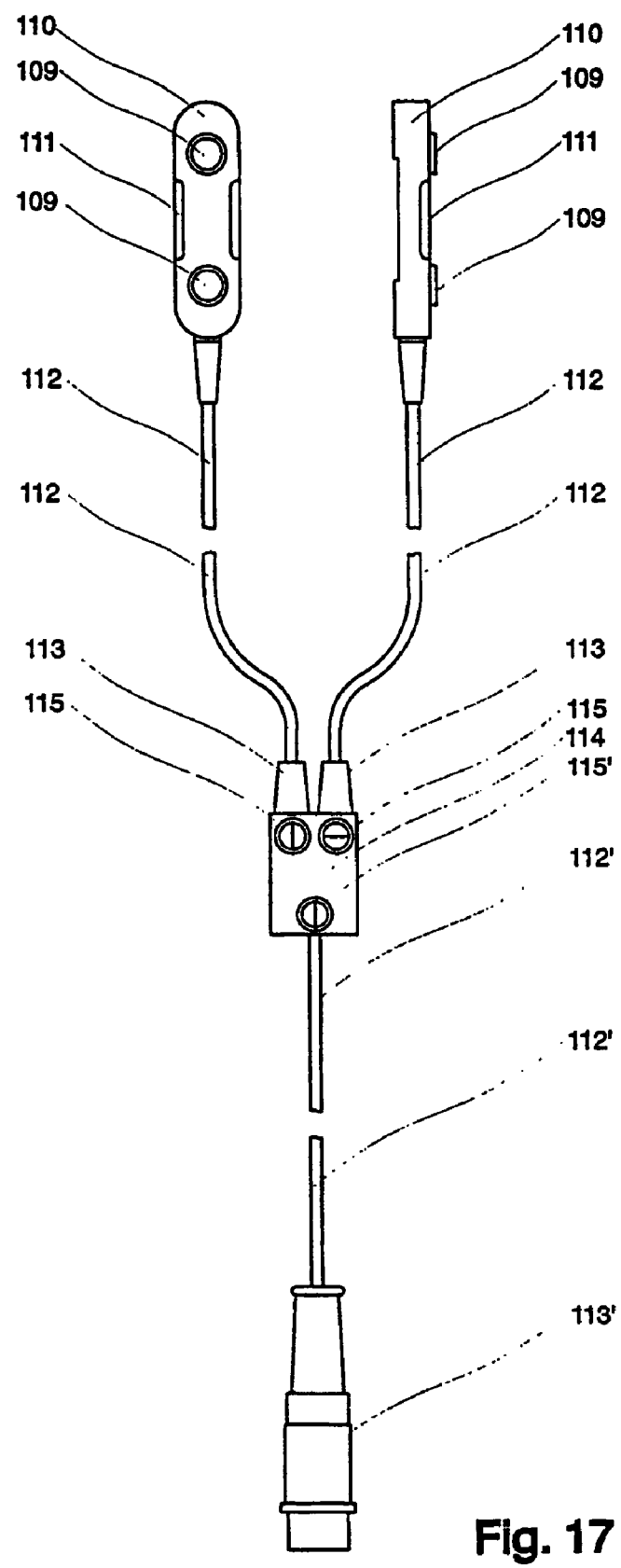
FIG. 17 shows: a pair of twin stimulation electrodes for stimulation of the examined nerve and muscle areas.

The stimulation of the motor system for examination, and especially for the examination of the ability of the muscles to function and perform, takes place in the area to be examined—for example, the hand—of the person to be tested, through a stimulant, which will trigger contractions. This can take place as a voluntary trigger, a central or peripheral magnet stimulation, a reflex stimulation through quick weight changes or muscle length changes or through a peripheral electrical stimulation. The quick weight or muscle length changes through the power source, under the conditions of the securing element unit and the stopping mechanisms as shown above, make it possible, for the first time, to adjust and repeat reflex triggers. As a more beneficial version of the electrical stimulation model, FIG. 17 shows a pair of twin-stimulation electrodes (109), in which two stimulation electrodes (109) are mounted on the plate (110); they are connected to a small switchbox (114) through a cable and plug (112 & 113). This small switchbox (114) has a single switch (115) for each pair of stimulation electrodes (109) as well as a main switch (115'). One or both pairs of the stimulation electrodes can, alternatively, be turned on or off with these switches. The pairs of stimulation electrodes are further connected to the electronic control unit of the device (not shown in FIG. 17), through the cable (112') and the connector plug (113').

Instead of the pairs of twin electrodes (109 & 110), only one pair of electrodes can be chosen according to the invention. Equally, though not as beneficial, one electrode on its own or as twin electrodes (109) can be used instead of a pair of stimulation electrodes (109).

FIG. 18 to 22 shows various mounting devices for fitting the stimulation electrodes in a non-tilting and non-movable way, especially showing the fitting of stimulation electrodes (109) to the necessary area of the body of the person being tested for stimulation of the motor system. The pair of stimulation electrodes (109) is placed into a small mounting block (116), which has—on its side turning away from the stimulation electrodes and the surface of the examined body parts—an elastic, but mostly rigid mounting lip (117), which protrudes over the small mounting block (116) on both sides. With this mounting lip (117), it sits in the mounting pockets (118) of a soft-elastic fastener (119). The fastener, with the attached stimulation electrodes (109), will be placed on the area of the body where stimulation is necessary, for example, the forearm with a clamp fastener (120), which is smoothly adjustable and removable.

Figure 21:
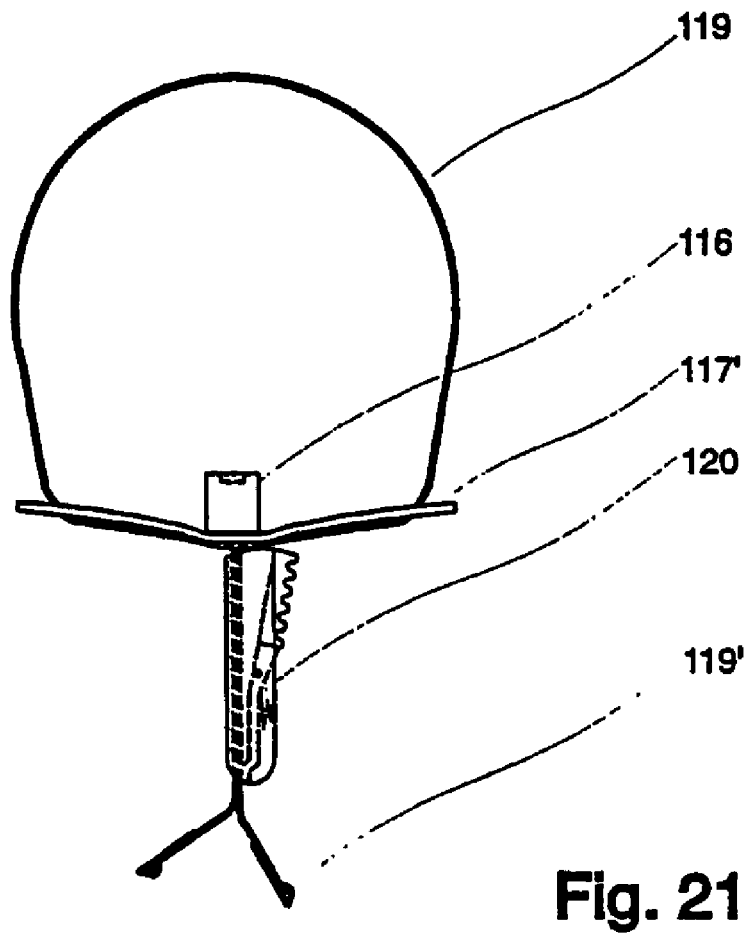
FIG. 21 shows: a modified mounting device, viewed from the side.

The clamp fastener (120) has a fastening opener (121) with a clamp axle (122) and a clamp spring (124), as visible in FIGS. 19 to 21. When using the fastening opener (121), the clamp (123) opens, so that the fastener (119) can be pushed through, adjusted in its length or pulled out completely. After attaching and adjusting the fastener with its pair of stimulation electrodes (109), they will be held in place by the clamp fastener (120), with the intended pressure applied. Removing the fastener without using the fastening opener (121) is not possible, however tightening of the tension of the fastener (119) is.

The fastener (119) has useful strengthening and stiffening on both ends, for easier insertion of the ends of the fixation band into the clamp fastener (120).

Figure 22:
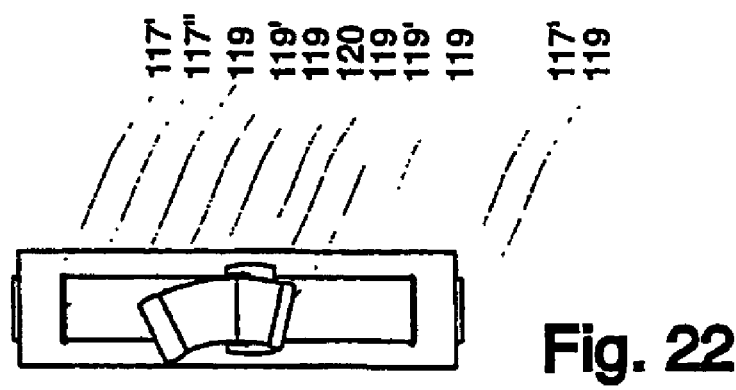
FIG. 22 shows: a detail from FIG. 21, featuring the wider mounting lip with the adjustable fastener threaded through it.

An altered version of the mounting device for the pair of stimulation electrodes (109, 110) is shown in FIGS. 21 and 22. The fastener (119) does not have the mounting pockets (118); the mounting lip (117') is therefore wider than the fastener (119) and has slits (117') on its two ends—which are the same width as the fastener (119)—through which the fastener is being pulled and then the ends are inserted into the clamp fastener (120). The clamp fastener (120) can be situated on any chosen point of the fastener (119). Shown in FIGS. 23 to 25, as well as 26 to 28, are small mounting blocks (116, 116'), at different heights for the stimulation electrodes (109, 110), which are each fitted to the mounting device and switchable and can be chosen according to the area of the body intended for stimulation. With this, the pressure to the stimulation electrode plate (110) and therefore the stimulation electrodes, can be varied and they can be pushed into the tissue of the examined limb at varying depths. Determining the results after examination, which are the basis for the electronic or other analysis, will be done either through the sensors of mechanical functioning, the dynamometer, the acceleration meter, the potentiometer or through the sensors for thermal and electrical functions. The mechanical sensors are, with the exception of the vibration meter, integrated as components of the invention device and are apparent in the drawings of the different versions of the invention devices in FIGS. 1 to 5, 15 and 16. They have already been in part mentioned in the description above. The dynamometer (237), according to FIG. 1, is, for example, built as a bending beam measuring gauge and measures the strength, as well as its time changes, to the thumb bridge (14) and, therefore, the strength of the muscle. The dynamometer (238) on the main unit axle (1), for example, as a torque meter, measures the power at the main unit axle (1) between the energy source (188, 189 or 190) and the axle stopping mechanism (125) and therefore, at the same time, the residual weights supported by the stopping mechanism, before they influence the muscle. The potentiometer (239 or 239') measures the position of the main unit axle (1) and, therefore, the length of the muscles being examined and the speed of their changes in length. The acceleration meter (140) on the thumb bridge adjuster (47 or 93) measures the acceleration of the muscle contractions and the muscle relaxation.

Figure 29:
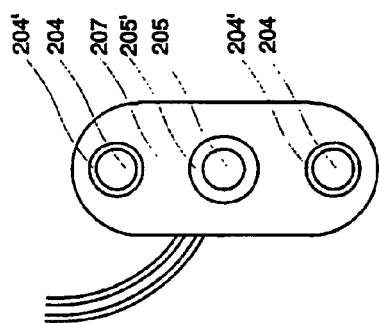
FIG. 29 shows: a sensor casing with sensors for the recording of electric and acoustic signals or vibrations, viewed from below.
Figure 30:
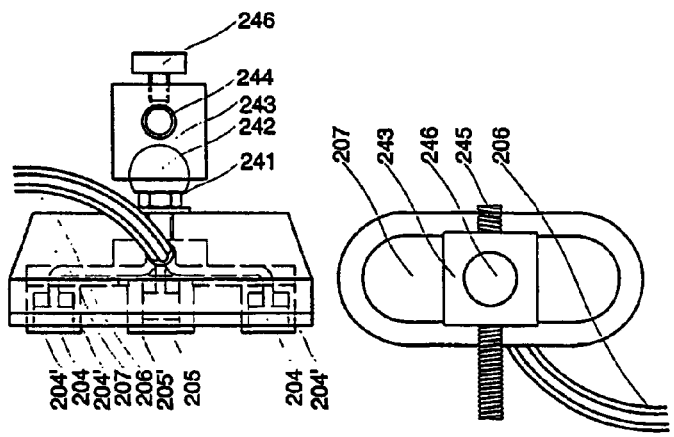
FIG. 30 shows: the sensor casing with sensors as in FIG. 29, viewed from the side.
Figure 31:
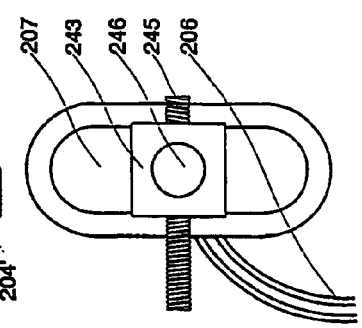
FIG. 31 shows: as a detail of FIG. 30, the ball and socket mount for the sensor unit.

The other sensors are brought into contact with the person being tested. Shown in FIGS. 29 to 31 are a combination of sensors for the recording of electrical potential fluctuations, the skin temperature and acoustic signals or vibrations as component parts. In the sensor casing (207) are, on the lower level, which is meant for placing on the body being examined, two electrode plates/thermal sensors (204), for measuring electrical potential fluctuations and the skin temperature. They are placed into a recess for the electrode (204'), which—at the same time—serves to hold contact substances like gel or paste. Furthermore, on the same level, is a vibration sensor or microphone (205) with sound tube (205'), for the recording of sounds and vibrations of the body area being examined. The sensors (204, 205) are connected to the amplifier and analysis electronics—which is not shown here—through the cable (206).

Figure 32:
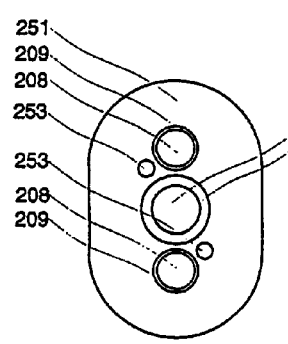
FIG. 32 shows: a modification of the sensor unit as in FIG. 29 with adhesive surfaces and vacuum connectors, viewed from below.
Figure 33:
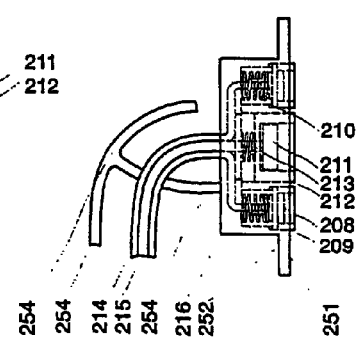
FIG. 33 shows: the sensor unit as in FIG. 32, a section in side view.
Figure 34:
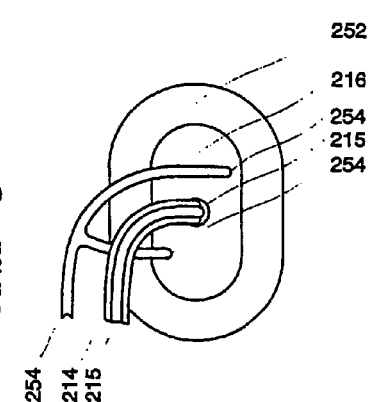
FIG. 34 shows: the sensor unit as in FIG. 32, viewed from above.

FIGS. 32 to 34 shows an amended version of the sensor unit according to FIGS. 29 to 31. The sensors (208, 209) basically correspond to the sensors (204, 204') and are for the recording of electric potential fluctuations and the skin temperature. The sensor (211, 212) is a vibration sensor or microphone-like sensor (205, 205'). However, these sensors each have differential springs (210 or 213) in the sensor casing, through which small, uneven patches or changes in the supporting surface (skin) of the person being examined, can be balanced, whilst maintaining an all-round, definable pressure to it. The sensor unit has, additionally, on its underside or, if preferred, its upper side, self-adhesive patches (251, 252) to be stuck to the body area being examined, which preferably should cover the whole edge area of the underside of the sensor unit. Furthermore, there are drill holes (253) through the casing from the underside of the sensor unit, which are intended for the connection of the sensor unit to a vacuum unit through the supply pipes (254), making possible a safe placement of the sensor unit on the body with the vacuum.

Figure 35:
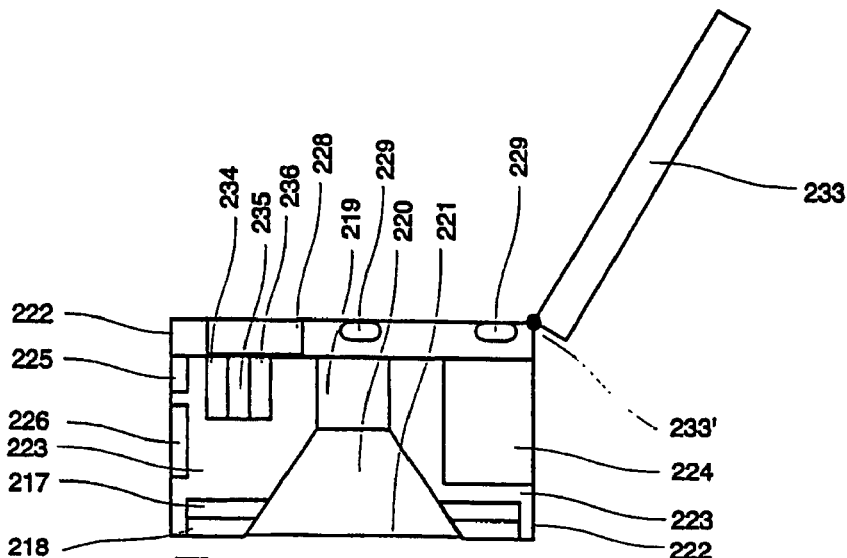
FIG. 35 shows: a multi sensor unit with a device for displaying, storage and processing of the measured results, viewed lengthways from one of the exterior sides.
Figure 36:
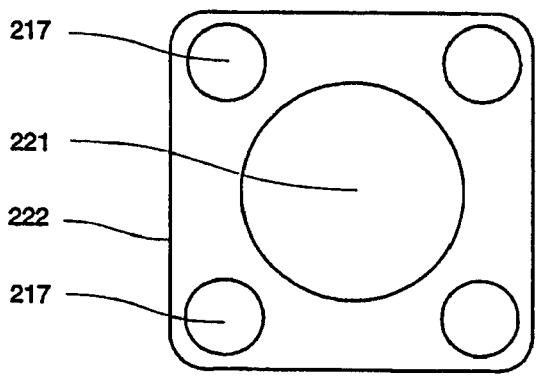
FIG. 36 shows: the multi sensor unit as in FIG. 35, viewed from below.
Figure 37:
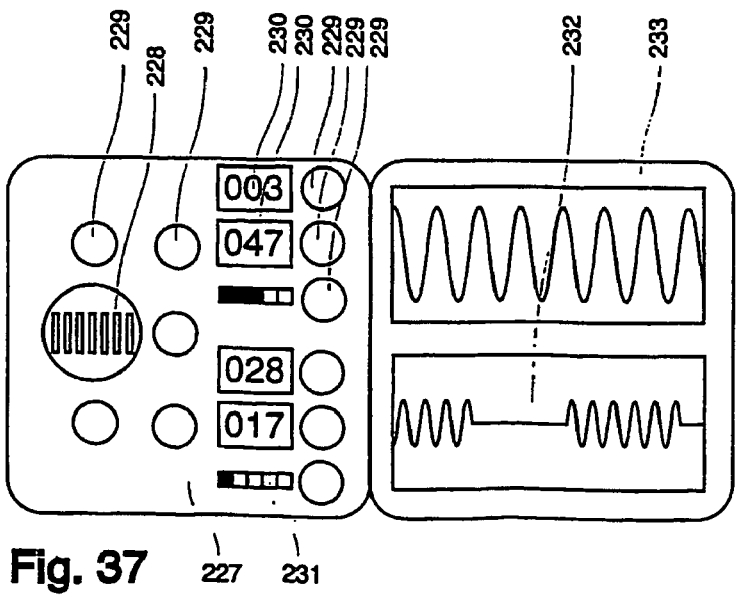
FIG. 37 shows: the multi sensor unit as in FIG. 35, viewed from above, with the operating and display areas.

FIGS. 35 to 37 show a multi-sensor unit (217 to 236) with integrated devices for the display, storage and processing of the recorded measurements, which are the subject of a separate Patent Claim by the Claimant and, therefore, a detailed description of these has not been included here.

If in the description above, single features/characteristics of the device and its components, which are illustrated in the drawings, but have not been mentioned especially, as they are not essential to the invention, they will be referred to in the listing of the reference numbers of the single parts of the device, which is an integral part of the registration.

The described invented device including further developments, provides the following advantages against already known devices. Definable and fully automated, constant, experimental splinting and securing of the motor system and especially of the muscles are made possible, through the definable and repeatable limitation of the muscle lengths and through the constant and repeatable use of weights The rest- and securing element with the splint rest and with the arm rest table in the described version, makes it possible to repeat examinations through re-positioning of the rest- and securing element and of the body parts being examined, through the automatic setting of the measurements and results previously made and stored.

The device makes it possible, to examine a body part, especially the human hand, in various positions, by attaching a supporting thumb mould, before or behind the thumb, depending on whether there should be more room for manoeuvrability between the thumb and hand towards the front or the back. The limb, with the palm of the hand upwards or downwards, can also be secured or fixed in a splint, depending on the manoeuvrability of the examined person and if the palm of the hand or the back of the hand should be more accessible. Additionally it is possible, with the same setting, to examine the agonist, for example, the thumb adductor, and the antagonist, for example, the thumb abductor. Through the device, the examination of the right and/or the left limb is alternatively made possible and different movement axles and therefore various muscle groups can be examined.

Through the invention device's automatic stopping mechanism, muscle length changes, over and/or under a certain length, are prevented, with which the muscle length conditions can be determined precisely, up to a certain point, before the start of the experiment.

Also, the type of contraction can be determined through the positioning of the described stopping mechanisms, that is, if the muscle carries out a sheer weight-lifting contraction (isometric) or a if pure contraction or shortening takes place (isotonic) or if the muscle goes into a support or touch spasm.

Through the described power sources and their versions, definable weights can affect the muscle before and after lifting. The torque of the power source is regulated in such a way, that sources for error, through the mass of moving parts, torque fluctuations, elasticity and friction, will be eliminated or balanced. The described power sources have a broad performance spectrum and are, to a large extent, maintenance free.

Distortions during the course of the testing procedure are avoided and constant conditions throughout duration of the testing procedure, via the described construction of the eccentric moving parts on the main unit axle. In particular, there is no trace of position-dependent gravity influences and hardly any acceleration-dependent torque fluctuations, movement-dependent torque losses and/or vibrations.

The power source can even give off electric pulses which themselves—via reflex arches—lead to involuntary, standardised muscle contractions or muscle relaxations. Last, but not least, through the related stimulants in the form of stimulation electrodes as a magnetic coil stimulator or energy-pulse stimulator, involuntary, standardised muscle contractions can be triggered.

The invention claimed is:

1. A device for the examination of the motor system of the human or animal body, through the examination and determination of the ability of the muscular system to function and perform, comprising means for inserting, resting and securing body parts to be examined; means for repeating examinations of the same body parts in a same fixed position; a power source to put weight on muscle; means for stimulating or contracting the muscles or nerves, a rest and securing element with a splint rest or with an arm rest table; a thumb mould with thumb bridge and a thumb lever, in which the thumb lever is connected to a vertically arranged main unit axle, which connects to the power source; means for determining the type of contraction, to automatically limit the power via stopping mechanism, as well as stimulants for stimulation of muscles, nerves or the central nervous system; and means for measuring resulting physiological reactions and including mechanical and electrical/electronic measuring devices selected from the group consisting of dynamometers, acceleration meters, muscle-length meters, sensors for the recording of electrical potential fluctuations, the skin temperature and acoustic signals and vibrations, wherein when using the rest and securing element with the splint rest, it is fitted vertically on a diagonal casing wall of a casing of the device, and on that is an arm rest with connecting hand rest; arranged further to this, at a right angle to the splint rest and the arm rest, are the back of the hand support with the back of the hand cushion and the adjustment bar, which are vertically adjustable through this adjustment bar via an adapted slot of the splint rest; further there is, also at a right angle to the arm rest, an arm rest and on the hand rest is a wrist support, horizontally adjustable via a carrier and adjustment track and attached securely with a fastening screw; a palm of the hand support, in connection with the wrist support, runs on the same level and attached to it is a finger support for the fingers II-V, which is movable; the hand including the wrist is inserted and secured, so that the back of the hand support, including the back of the hand cushion is moved vertically through an electrical motor with an ammeter/cut out via a spindle, into which the adjustment bar with the small adjustment block meshes and that alternatively, the wrist support on the adjustment track is moved horizontally and locked in place with the adjusting screw; the motor and the spindle are arranged on the side of the splint rest away from the arm rest through spindle tracks and that the back of the hand support, with the connection bar, can be swivelled around a vertical axle via a swivel coupling in the area where the spindle meshes; the finger support is moved towards the index finger with the aid of a small adjustment block on an adjustment track and locked in place with the adjusting screws.

2. A device according to claim 1, wherein the vertically arranged main unit axle has the axle stopping mechanism between its connection with the thumb lever and the power source, which works together with the front rotation stopping mechanism for limiting physiological contractions and the rear rotation stopping mechanism for limiting physiological stretching, where the front rotation stopping mechanism is attached to an adjustment wheel through which the front rotation stopping mechanism is adjustable at an angle, and the rear rotation stopping mechanism is attached to an adjustment wheel, for adjustment at an angle.

3. A device for the examination of the motor system of the human or animal body, through the examination and determination of the ability of the muscular system to function and perform, comprising means for inserting, resting and securing body parts to be examined; means for repeating examinations of the same body parts in a same fixed position; a power source to put weight on muscle; means for stimulating or contracting the muscles or nerves; a rest and securing element with a splint rest or with an arm rest table; a thumb mould with thumb bridge and a thumb lever, in which the thumb lever is connected to a vertically arranged main unit axle, which connects to the power source; means for determining the type of contraction, to automatically limit the power via stopping mechanism, as well as stimulants for the stimulation of muscles, nerves or the central nervous system; mechanical and electrical/electronic measuring devices selected from the group consisting of dynamometers, acceleration meters, muscle-length meters, sensors for the recording of electrical potential fluctuations, the skin temperature and acoustic signals and vibrations, wherein the vertically arranged main unit axle has the axle stopping mechanism between a connection with the thumb lever and the power source, which works together with the front rotation stopping mechanism and the rear rotation stopping mechanism, wherein the front rotation stopping mechanism is attached to one adjustment wheel through which the front rotation stopping mechanism is adjustable at one angle, and the rear rotation stopping mechanism is attached to another adjustment wheel, for adjustment at another angle, wherein the one adjustment wheel, via a bearing, is placed on a guiding rod, which grips the main unit axle without pressure and is equipped with a sprocket, into which a cogwheel interlocks, which is driven by an adjustment motor through one axle, wherein the other adjustment wheel, via a bearing, is fitted on a guiding rod, which grips the main unit axle without pressure and the other adjustment wheel is equipped with a sprocket, into which a cogwheel interlocks, which is driven by an adjustment motor, through another axle wherein on the adjustment motor via an axle, a potentiometer is placed for measuring the position of the front rotation stopping mechanism and on the adjustment motor, via an additional axle, a potentiometer is placed for measuring the position of the rear rotation stopping mechanism.

4. A device for the examination of the motor system of the human or animal body, through the examination and determination of the ability of the muscular system to function and perform, comprising means for inserting, resting and securing body parts to be examined, with means to repeat for repeating examinations of the same body parts in a same fixed position, with a power source to put weight on muscle, as well as means for stimulating or contracting the muscles or nerves; a rest and securing element with a splint rest or with an arm rest table; a thumb mould with thumb bridge and a thumb lever, in which the thumb lever is connected to a vertically arranged main unit axle, which connects to the power source; means for determining the type of contraction, to automatically limit the power via stopping mechanism, as well as stimulants for the stimulation of muscles, nerves or the central nervous system; mechanical and electrical/electronic measuring devices selected from the group consisting of dynamometers, acceleration meters, muscle-length meters, sensors for the recording of electrical potential fluctuations, the skin temperature and acoustic signals and vibrations, in that, when using the power source in form of a linear motor or lifting magnets, a front axle stopping mechanism is placed on a linear axle connecting to the power source, which forms a stopping mechanism for a front linear stopping mechanism, positioned diagonally to the linear axle, and a rear axle stopping mechanism placed on the linear axle, which forms a stopping mechanism for the a rear linear stopping mechanism, also positioned diagonally to the linear axle; hereby, the linear stopping mechanisms each consist of a bridge, which is guided by vertically positioned guiding rods and rests on the latter, via glide bearings, which are adjustable parallel to the linear axle, where the adjustment of the front linear stopping mechanism, occurs through a motor via one spindle and the adjustment of the rear linear stopping mechanism occurs through a motor via another spindle; one potentiometer for measuring the position of the front linear stopping mechanism, is placed on the one spindle and another potentiometer for measuring the position of the rear linear stopping mechanism, is placed on the other spindle.

5. A device according to claim 1, wherein the splint rest is fitted horizontally and parallel to the dividing wall of the device casing and is movable/adjustable on one or more guide tracks, which are fitted to the dividing wall with mountings and arranged as spindles by means of an electrical motor.

6. A device according to claim 1, wherein with the rest- and securing element and the arm rest table, the table is horizontally movable on tracks, parallel to the diagonal casing wall, above which, the arm rest table is guided by a spindle and powered by a motor, which is installed below the arm rest table on the diagonal casing wall via a small connection block, which is firmly attached to the underneath of the arm rest table and guided in a spindle with spindle tracks on the underneath of the arm rest table and is being moved towards the spindle by a transmission belt; the device is characteristic further, in that an arm rest is fitted centrally for placing the arm and hand for both sides, on which an arm clamp cushion, with fastening clamp and clamp bracket, is fitted to its top side and, a distance apart from it, a palm of the hand clamp cushion with fastening clamp and clamp bracket, which can—with screws, in rows with the holes—each be shifted lengthways of the arm rest, through which the arm clamp cushion and the palm of the hand cushion can also be shifted by 180° in order to secure the respective inserted arm and hand; the arm clamp cushion is adjustable in height by means of a guide bar with a locking mechanism, and the palm of the hand clamp cushion, by means of a guide bar with a locking mechanism, for the adjustment of the palm of the hand and arm; further to this, there is, on both sides of the arm rest on the arm rest table, a movable finger support, which has a swivel coupling with swivel coupling pin, through which, together with an elongated hole in the arm rest table, is a connection to a small adjustment block, which leads, through a spindle with counter-rotating threads and a motor with transmission belt for the spindle, the finger supports are running opposite towards the splint to the respective inserted hand, where the spindle, with spindle tracks, as well as the motor, are attached to the underneath of the arm rest table; further to this, there are, relating to the finger supports, intended for the support of the outer side of the arm in the area of the arm clamp cushion, on both sides of the arm rest, arm supports with swivel coupling, the swivel coupling pin, the small adjustment block, the spindle with spindle tracks and the motor with transmission belt, which together will move towards the inserted arm.

7. A device according to claim 6, wherein to support the finger tips on the rest- and securing element with arm rest table, a movable support is placed on that table, with a small adjustment block, guided into a spindle with spindle tracks on the arm rest table, which is moved by a motor with a transmission belt and moves the support on telescopic tracks towards the finger tips of the hand to be examined hand which is secured in place.

8. A device according to claim 1, wherein the rest- and securing elements or can be interchanged, and be used as separate modules of the device, or other splint rest elements, where they should preferably be separated from the remaining devices by a double casing wall.

9. A device according to claim 1, wherein for the finger to be examined or thumb of the inserted hand, a thumb mould with the thumb bridge or else the thumb mould with the thumb bridge, are available, whereby the thumb bridge connects to the horizontally placed thumb lever and is horizontally movable by means of an adjustment device with locking mechanism.

10. A device according to claim 1, wherein positioned on the top end of the main unit axle, is a light beamer, preferably a laser direction-finding beamer with an aperture, whose direction-finding beam is pointed to the body part to be examined and is aligned with its movement axle before securing.

11. A device according to claim 1, wherein instead of or additionally to, the laser direction-finding beamer, a laser direction-finding beamer is arranged at the end of a swivel arm, which with its other end can swivel and is attached to the track of the arm rest table and will be swivelled over the body part resting in it and being examined, in which the laser direction-finding beamer and its direction-finding beam, are aligned, whilst in the position that it has been swivelled into, with the main unit axle- and matched up with it, whereby the movement axle of the body part to be examined, is brought into alignment with the direction-finding beam, before securing.

12. A device according to claim 1, wherein with the rest- and securing element and arm rest table, the table is horizontally movable in the tracks, parallel to the diagonal casing wall; a cast, made from synthetic or other material, is used as a negative form for the resting and securing of the hand to be examined, and will be inserted into the corresponding drill holes of the arm rest table, by means of the imbedded spacing pins, which protrude on the underneath of the cast in such away, that the movement axle of the hand will be aligned with the main unit axle of the device and the cast will have a cavity cut out in the area of the thumb and the thumb muscle, for the thumb mould with a thumb bridge, so that the thumb can be positioned and will have a connection to the thumb lever and the main unit axle.

13. A device according to claim 12, wherein for the making of the cast, a mould is used, with spacing pins at the bottom of it, which can be removed; a laser direction-finding beamer, with a swivel arm, is positioned on one of the top outer rims of the mould, whereby for the making of the cast, the hand is placed with the back of the hand onto the spacing pins, then the laser direction-finding beamer is swivelled over it and its direction-finding beam aligned with the movement axle of the hand, as the mould with the hand in it, will be filled in with suitable plastic or other hardening pouring substance.

14. A device according to claim 1, further comprising have a rest plate for resting and securing those body parts with big joints which has a fastening ring with a locking mechanism for this ring for firmly fastening onto the main unit axle, whereby a fastener is additionally attached to the rest plate, as well as a measuring scale at the elongated hole for measuring the position of the body part being examined.

15. A device according to claim 1, characteristic in that a rotation magnet with constant or constantly increasing indicator line is used as a power source.

16. A device according to claim 1, wherein two rotation magnets are used as the power source, preferably with a constant total or a constantly increasing indicator line, which are switched, one after the other, and are being rotated around the inner part connected to the main unit axle, whilst a sprocket is positioned between the rotation magnets—which is connected to a motor through a rack track with a track bearing, a cog wheel and a transmission belt which adjusts the rotation magnets; a potentiometer is fitted to the motor for measuring the position of the rotation magnets.

17. A device according to claim 1, wherein an electric motor is used as a power source, preferably in the form of a Hall motor.

18. A device according to claim 1, wherein a linear drive, in the form of a linear motor or lifting magnet, is used as the power source, which transmits power through the linear axle and a transmission/power diversion onto the main unit axle, positioned at a right angle to the linear axle; a transmission wheel sits firmly on the main unit axle in the area of the linear axle and with a transmission cord, half of which is running on top of the transmission wheel to the lower cord clip on the linear axle and will be fixed in place, and the other half is running under the transmission wheel to the upper cord clip on the linear axle and will be fixed in place; attached on the side opposite the transmission cord of the linear axle, is a counter-moving cord with clamps, which are themselves connected to the linear axle via clamp bridges, to avoid one-sided strain and bending of the linear axle; the linear axle is resting on a guiding bar, with glide bearing and with its end opposite the power source.

19. A device according to claim 1, wherein the stimulation of the motor system of the person being examined, takes place in the form of voluntary triggers, central and peripheral magnetic stimulation, reflex stimulation—preferably through changes of the muscle length through the power source or as peripheral electrical stimulation through stimulants with stimulation electrodes.

20. A device according to claim 19, characteristic in that the stimulation electrodes are used as a pair of twin-stimulation electrodes, each pair having mounting plates, with two stimulation electrodes inserted and each pair of electrodes is connected to a small switch box via a cable and plug, which has a single switch for each pair of stimulation electrodes and a main switch; the pairs of stimulation electrodes are connected to the control electronics of the control unit device through a cable and plug.

21. A device according to claim 20, wherein the stimulation electrodes, with the mounting plate, are placed into a small mounting block, which has—on the off side of the stimulation electrodes—an elastic, but mostly rigid mounting lip, with which it sits in the mounting pockets of a fastener; the fastener with the small mounting block and the stimulation electrodes, will be placed on the body part to be examined by means of a clamp fastener, which can be operated with one hand and is smoothly adjustable and removable.

22. A device according to claim 21, wherein the mounting device for the pair of stimulation electrodes has a mounting lip—for the small mounting block, with stimulation electrodes—which is wider than the fastener and has slits on its two ends, through which the fastener is being pulled through.

23. A device according to claim 21, wherein the small mounting blocks have different heights, so that they can be adjusted to the body area to be stimulated.

24. A device according to claim 1, wherein a dynamometer is attached to the thumb bridge, which measures the power exerted on the thumb bridge and its time changes, and therefore measures the strength of the muscle.

25. A device according to claim 1, wherein a dynamometer is attached to the main unit axle (1), which measures the strength on the main unit axle between the power source and the axle stopping mechanism, and therefore measures the residual weights supported by the axle stopping mechanism and the rotation stopping mechanism before they affect the muscle.

26. A device according to claim 1, wherein the dynamometer is attached to the linear axle, which measures the power between the linear motor or the linear stopping mechanism and the transmission/power diversion of the main unit axle.

27. A device according to claim 1, wherein a potentiometer is attached to the main unit axle or a potentiometer with transmission cord to the linear axle, which measures the position of the main unit axle and the length of the examined muscles, as well as the speed of the muscles' change in length.

28. A device according to claim 1, wherein an acceleration meter on the thumb bridge adjustment of the thumb bridge, measures the acceleration of the muscle contraction and the muscle relaxation.

29. A device according to claim 1, wherein electrical/electronic sensors are included, for the recording of electrical potential fluctuations, the skin temperature and acoustic signals and vibrations, which are being brought into direct contact with the body parts being examined.

30. A device according to claim 29, wherein the sensors for the recording of electrical potential fluctuations, and of the skin temperature, are in the form of small electrode plates, which are inserted into the recesses for the small electrode, which are used at the same time hold contact substances; that the sensor for the recording of acoustic signals or vibrations is a vibration sensor or microphone with a sound tube, which are each connected to an amplifier and analysis electronics.

31. A device according to claim 1, wherein at least one sensor, as well as a sensor in the casing, is integrated and positioned on the bottom level of the casing—which is intended for resting on the body of the person to being examined—and that the casing is positioned, so that it is movable on the splint rest or on the arm rest table.

32. A device according to claim 1, wherein the sensors for the recording of electrical potential fluctuations and the skin temperature, as well as sensors for the recording of acoustic signals or vibrations, are equipped with differential springs in the sensor casing; further that the casing has self-adhesive patches on its underside side and preferably also on one of the rim areas of the side facing away from the body part being examined, and that drill holes from the underside of the casing lead to pipe connectors on a vacuum unit.

33. A device according to claim 1, wherein during the examination, a multi-sensor unit is being used, in which, apart from sensors, there are also integrated devices for the display, storage and processing of the recorded measuring results.

34. A device according to claim 1, wherein a slip clutch mechanism, which is adjustable in its working area, is attached to the main unit axle in connection with the rotation magnets.

35. A device according to claim 1, wherein the thumb lever is connected to the main unit axle by means of a pin with a predefined breaking point, where the pin breaks when a defined limited of the power source is exceeded.

36. A device according to claim 1, wherein a measuring scale for the adjustment unit is connected to the thumb lever.

37. A device according to claim 1, wherein a linear meter for measuring the position of the armrest table, is attached to the small adjustment block of the armrest table.

38. A device according to claim 1, wherein a linear meter for measuring the position of the finger support is attached to the small adjustment block.

39. A device according to claim 1, wherein a linear meter for measuring the position of the arm support is attached to the small adjustment block of the arm support.

40. A device according to claim 1, wherein a linear meter for measuring the position of the fingertip support, is attached to the fingertip support.

41. A device according to claim 1, wherein elements selected from the group consisting of the rest and securing element and the thumb mould are adjustable to an anatomy of a human or animal body and fixable in an adjusted position.

42. A device according in claim 41, wherein said element selected from the group consisting of the rest and securing element and the thumb mould is configured so that it is adjustable in a manner selected from the group consisting of by an electric motor and manually and measured in an adjusted position for a repeated positioning.

43. A device according to claim 41, further comprising means for exact positioning of the rest and securing element relative to a motion axis of a muscle so as to align a physiological motion axis of the muscle exactly with the main unit axle.

44. A device according to claim 1, wherein said stopping mechanism is fixedly connected with said main unit axle.

45. A device according to claim 2, wherein the front rotation stopping mechanism and the rear rotation stopping mechanism are configured so that they operate independently from one another.

46. A device according to claim 2, further comprising means for measuring adjustments of the front rotation stopping mechanism and the rear rotation stopping mechanism for repeating the adjustments for further positioning.

47. A device according to claim 1, wherein the stopping mechanism is floatingly arranged on the axle.

48. A device according to claim 1, wherein the power source is adjustable independently of actual muscle contractions.

49. A device according to claim 48, wherein the power source is configured so that an inhomogeneous magnetic field does not influence small active muscle contractions resulting from friction and/or fluctuations of force.

50. A device according to claim 48, wherein the power source is configured so that a counterforce during acceleration and movement phases of the examination remain constant.

* * * * *